United States Patent
Krishna et al.

(10) Patent No.: US 12,002,569 B2
(45) Date of Patent: Jun. 4, 2024

(54) GENERATING MULTI-DIMENSIONAL RECOMMENDATION DATA OBJECTS BASED ON DECENTRALIZED CROWD SOURCING

(71) Applicant: Optum Technology, Inc., Eden Prairie, MN (US)

(72) Inventors: Amit Krishna, Bengaluru (IN); Rahul Dutta, Bengaluru (IN); Shubhendu Shekhar, Bengaluru (IN); Atul Kumar, Bangalore (IN); Love Hasija, Sonepat (IN)

(73) Assignee: Optum Technology, Inc., Eden Prairie, MN (US)

(*) Notice: Subject to any disclaimer, the term of this patent is extended or adjusted under 35 U.S.C. 154(b) by 532 days.

(21) Appl. No.: 17/143,004

(22) Filed: Jan. 6, 2021

(65) Prior Publication Data

US 2022/0215931 A1    Jul. 7, 2022

(51) Int. Cl.
*G16H 20/70* (2018.01)
*G06N 20/00* (2019.01)
(Continued)

(52) U.S. Cl.
CPC .............. *G16H 20/70* (2018.01); *G06N 20/00* (2019.01); *G16H 10/60* (2018.01); *G16H 40/63* (2018.01);
(Continued)

(58) Field of Classification Search
None
See application file for complete search history.

(56) References Cited

U.S. PATENT DOCUMENTS 8,930,204 B1   1/2015   Igoe et al.
9,849,364 B2   12/2017  Tran et al.
(Continued)

OTHER PUBLICATIONS

Mackey et al. "Fit-for-purpose?'—challenges and opportunities for applications of blockchain technology in the future of healthcare", 2019, BMC Medicine (2019) 17:68 (Year: 2019).*
(Continued)

*Primary Examiner* — Evangeline Barr
*Assistant Examiner* — Anne-Marie K Alderson
(74) *Attorney, Agent, or Firm* — Alston & Bird LLP

(57) ABSTRACT

Various embodiments provide for decentralized crowd sourced generation of recommendation data objects. An example apparatus receives, originating from an external computing device, a recommendation data object request, the recommendation data object request comprising a user identifier and one or more user attributes. The example apparatus may further retrieve, based on a predictive recommendation model, one or more therapy identifiers associated with a therapy efficacy score exceeding a therapy efficacy score threshold for attributes of a first attributes set associated with a first cluster identifier, the first attributes set comprising one or more of the one or more user attributes. The predictive recommendation model is trained based at least in part on trusted efficacy blocks of a distributed ledger, where the trusted efficacy blocks are added to the distributed ledger when a number of therapy efficacy transaction blocks associated with a given therapy identifier and having a therapy efficacy score exceeding a therapy efficacy score threshold meets or exceeds a therapy efficacy transaction block threshold. The example apparatus may further transmit, to the external computing device, a recommendation data object configured for rendering for display via a display device of the external computing device, where the recom-
(Continued)

mendation data object comprises one or more of the one or more therapy identifiers.

22 Claims, 15 Drawing Sheets

(51) Int. Cl.
    *G16H 10/60*      (2018.01)
    *G16H 40/63*      (2018.01)
    *G16H 50/20*      (2018.01)
    *H04L 9/06*      (2006.01)
    *H04L 9/00*      (2022.01)

(52) U.S. Cl.
    CPC ........... *G16H 50/20* (2018.01); *H04L 9/0643* (2013.01); *H04L 9/50* (2022.05)

(56) References Cited

U.S. PATENT DOCUMENTS

| | | | |
|---|---|---|---|
| 10,252,058 B1 | 4/2019 | Fuerst | |
| 10,463,271 B2 | 11/2019 | Intrator | |
| 10,531,806 B2 | 1/2020 | Principe et al. | |
| 10,560,272 B2 | 2/2020 | Yang et al. | |
| 10,631,743 B2 | 4/2020 | Goldberg et al. | |
| 2004/0172299 A1* | 9/2004 | Paul | G16H 50/20 705/2 |
| 2013/0022951 A1* | 1/2013 | Hughes | G16H 20/60 434/262 |
| 2016/0055760 A1 | 2/2016 | Mirabile | |
| 2017/0116379 A1* | 4/2017 | Scott | G16H 50/20 |
| 2017/0238859 A1 | 8/2017 | Sadowsky et al. | |
| 2018/0246570 A1 | 8/2018 | Coleman et al. | |
| 2018/0285528 A1 | 10/2018 | Healey et al. | |
| 2019/0209022 A1* | 7/2019 | Sobol | A61B 5/0022 |
| 2019/0246936 A1 | 8/2019 | Garten et al. | |
| 2019/0295436 A1* | 9/2019 | Rubinstein | A61B 5/1121 |
| 2019/0362376 A1* | 11/2019 | Newell | G06Q 20/3829 |
| 2019/0392924 A1* | 12/2019 | Bettencourt-Silva | G16H 50/70 |
| 2020/0077942 A1 | 3/2020 | Youngblood et al. | |
| 2020/0242354 A1* | 7/2020 | Ligman | H04L 9/0637 |
| 2020/0251213 A1 | 8/2020 | Tran et al. | |
| 2020/0273578 A1* | 8/2020 | Kutzko | G06N 20/00 |
| 2020/0273579 A1* | 8/2020 | Wright | G16H 20/30 |
| 2020/0294670 A1 | 9/2020 | Kotikela et al. | |
| 2020/0311108 A1* | 10/2020 | Kumar | G06F 16/287 |
| 2020/0322159 A1* | 10/2020 | Xu | H04L 9/3236 |
| 2020/0364243 A1* | 11/2020 | Tamayo-Rios | G06F 16/285 |
| 2020/0365266 A1* | 11/2020 | Jarvis | A61B 5/4815 |
| 2021/0374525 A1* | 12/2021 | Bremer | G06N 3/045 |
| 2021/0383927 A1* | 12/2021 | Godden | G06N 5/04 |
| 2022/0198304 A1* | 6/2022 | Szczepanik | G06F 16/2474 |

OTHER PUBLICATIONS

Ahn, Joong Woo et al. "A Novel Wearable EEG and ECG Recording System for Stress Assessment," Sensors, Apr. 28, 2019, vol. 19, No. 9, pp. 1-14. DOI: 10.3390/s19091991.

Leeming, Gary et al. "A Ledger of Me: Personalizing Healthcare Using Blockchain Technology," Frontiers in Medicine, vol. 6, No. 171, Jul. 24, 2019, pp. 1-10. DOI: 10.3389/fmed.2019.00171.

Mamoshina, Polina et al. "Converging Blockchain and Next-Generation Artificial Intelligence Technologies to Decentralize and Accelerate Biomedical Research and Healthcare," Oncotarget, vol. 9, No. 5, Nov. 9, 2017, pp. 5665-5690.

\* cited by examiner

GENERATING MULTI-DIMENSIONAL RECOMMENDATION DATA OBJECTS BASED ON DECENTRALIZED CROWD SOURCING

BRIEF DESCRIPTION OF THE DRAWINGS

Figure 1:
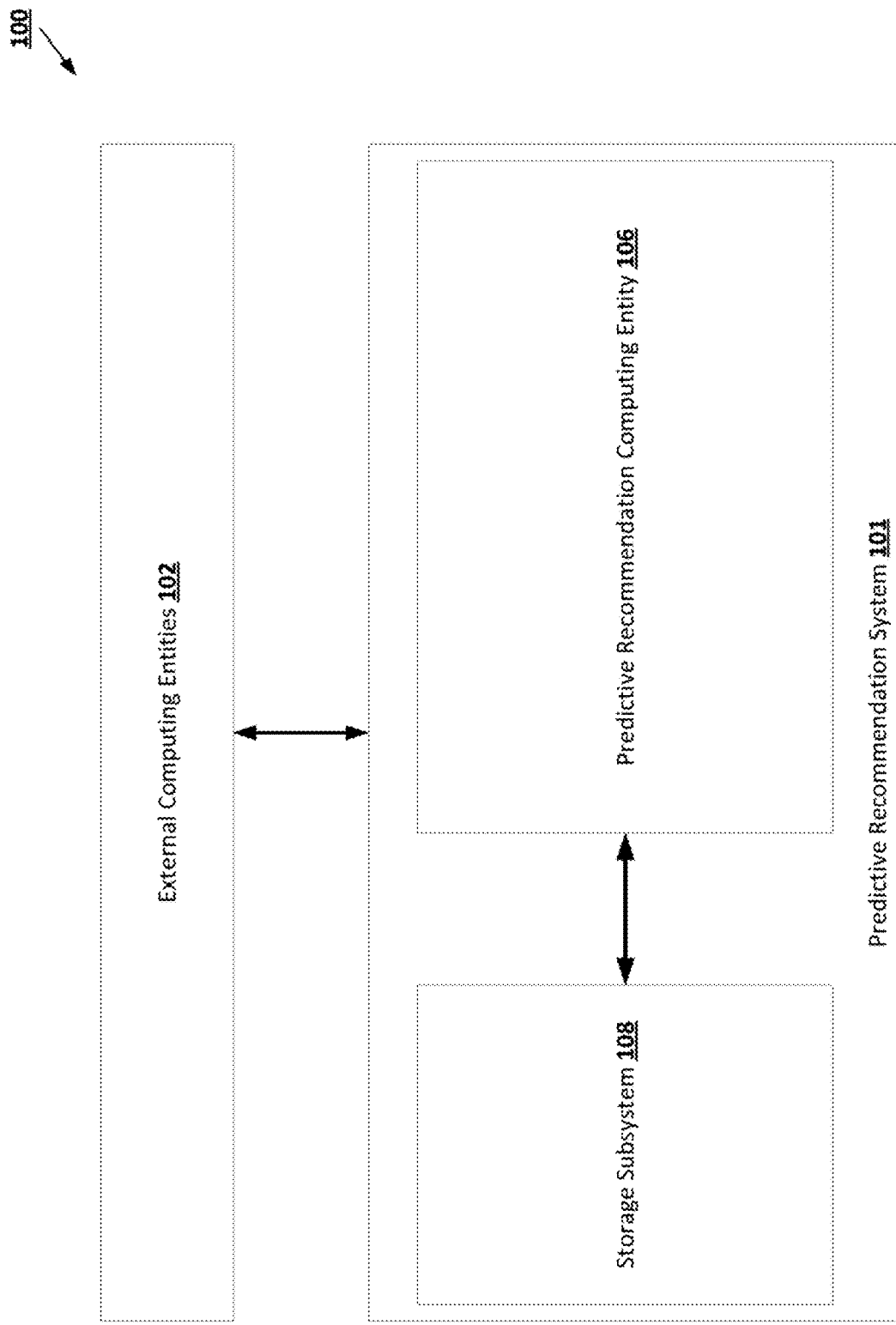

Having thus described the disclosure in general terms, reference will now be made to the accompanying drawings, which are not necessarily drawn to scale, and wherein:

FIG. 1 provides an exemplary overview of an architecture that can be used to practice embodiments of the present disclosure.

Figure 2:
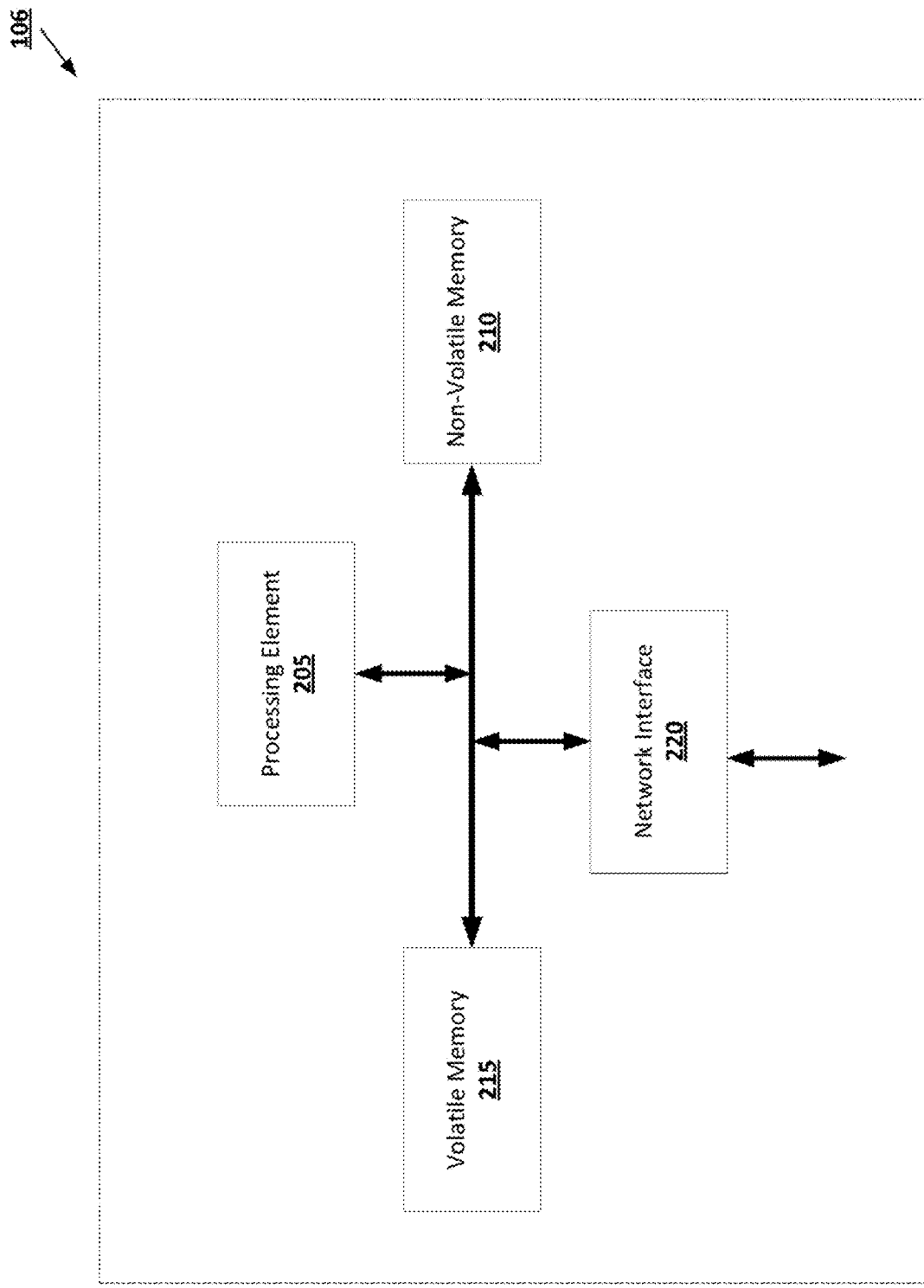

FIG. 2 provides an example predictive recommendation computing entity in accordance with some embodiments discussed herein.

Figure 3:
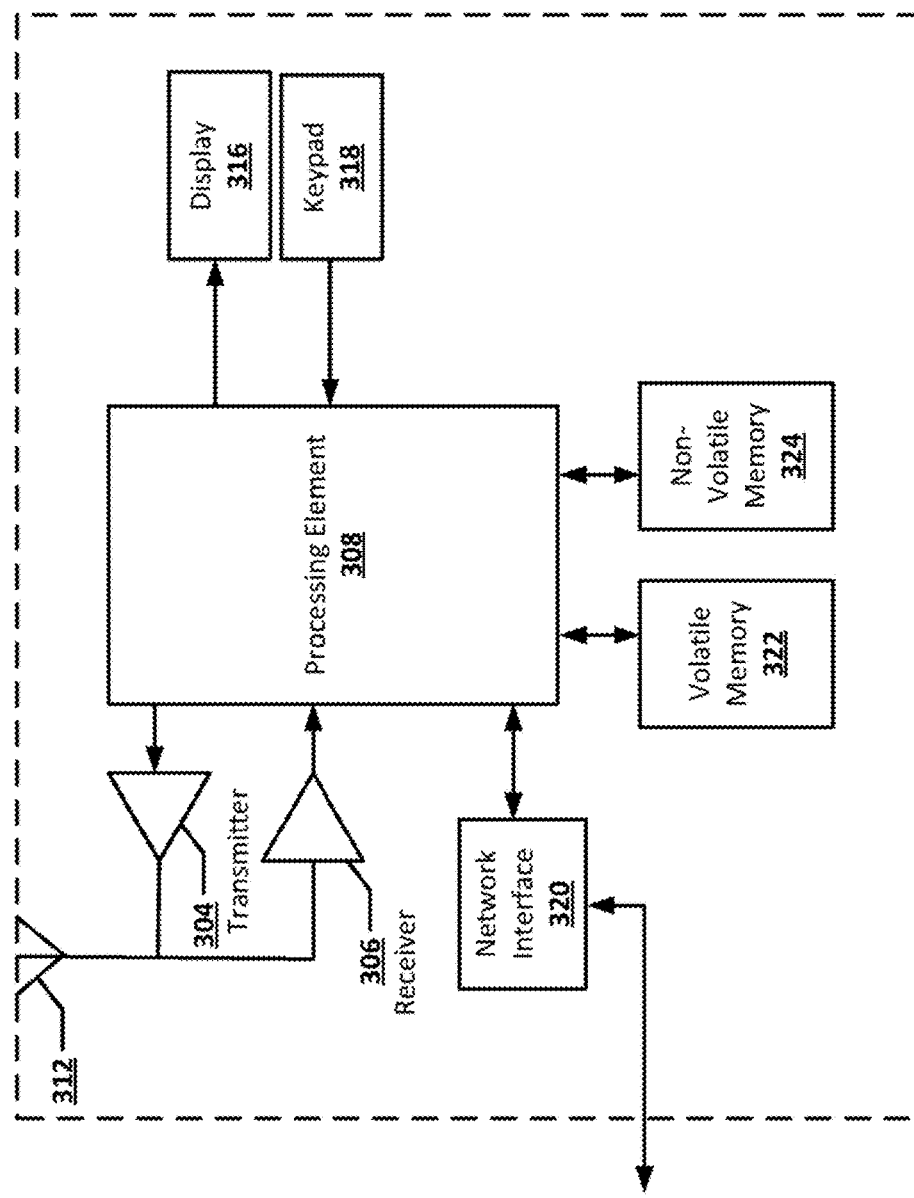

FIG. 3 provides an example external computing entity in accordance with some embodiments discussed herein.

FIGS. 4A, 4B, 4C, and 4D illustrate an example system data flow for use with embodiments of the present disclosure.

Figure 5:
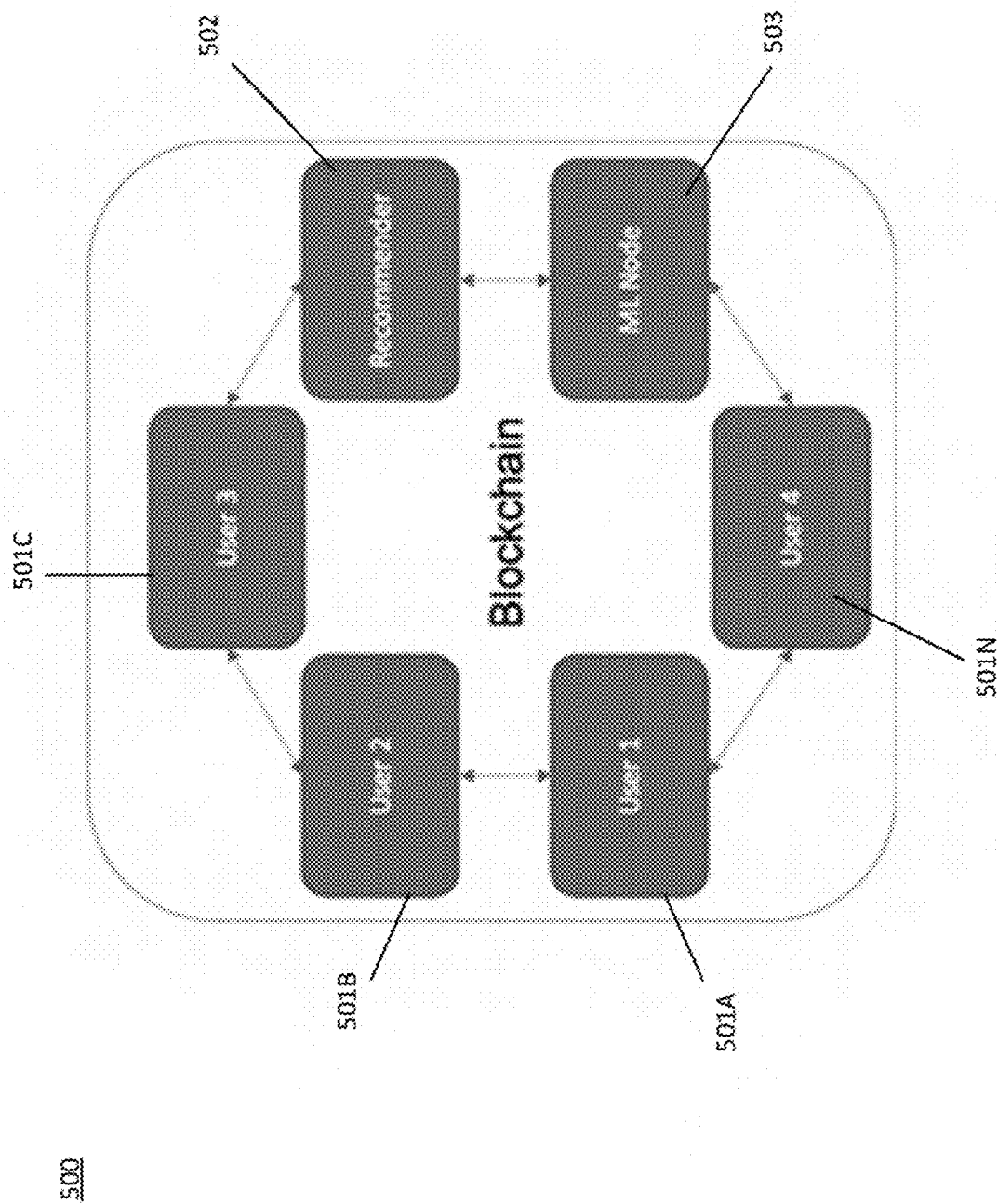

FIG. 5 illustrates an example block chain or distributed ledger network for use with embodiments of the present disclosure.

Figure 6A:
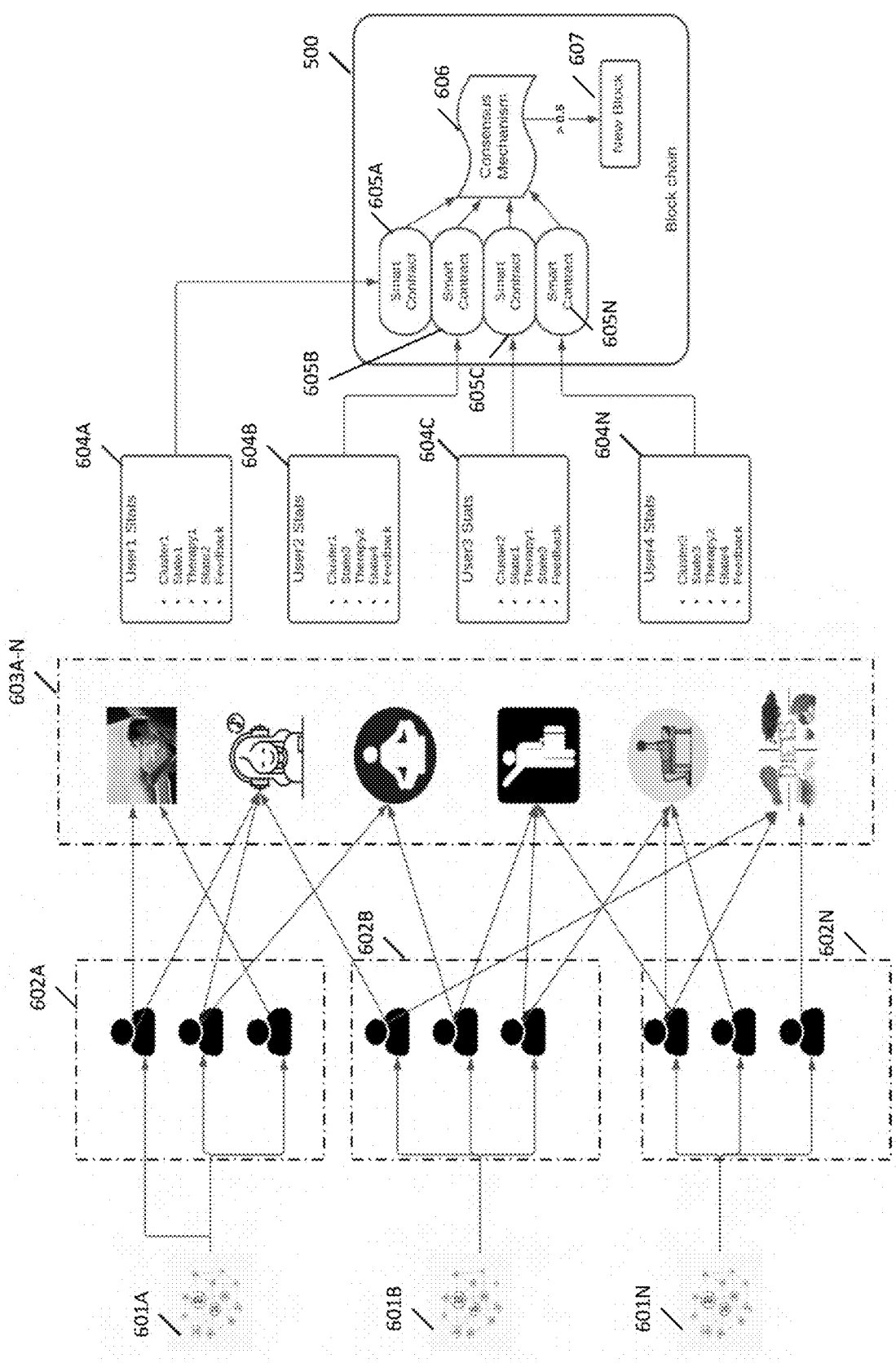
Figure 6B:
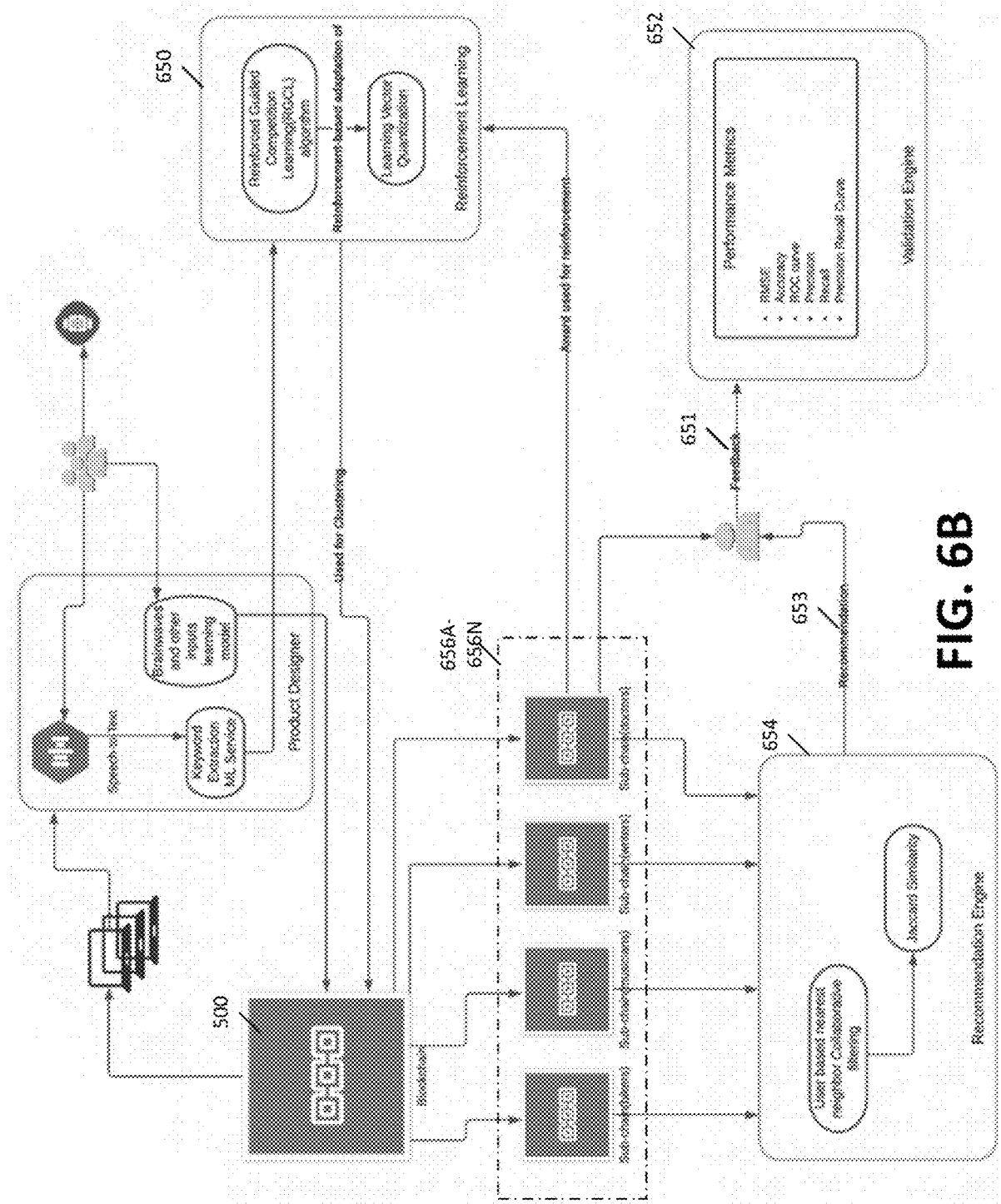
Figure 6C:
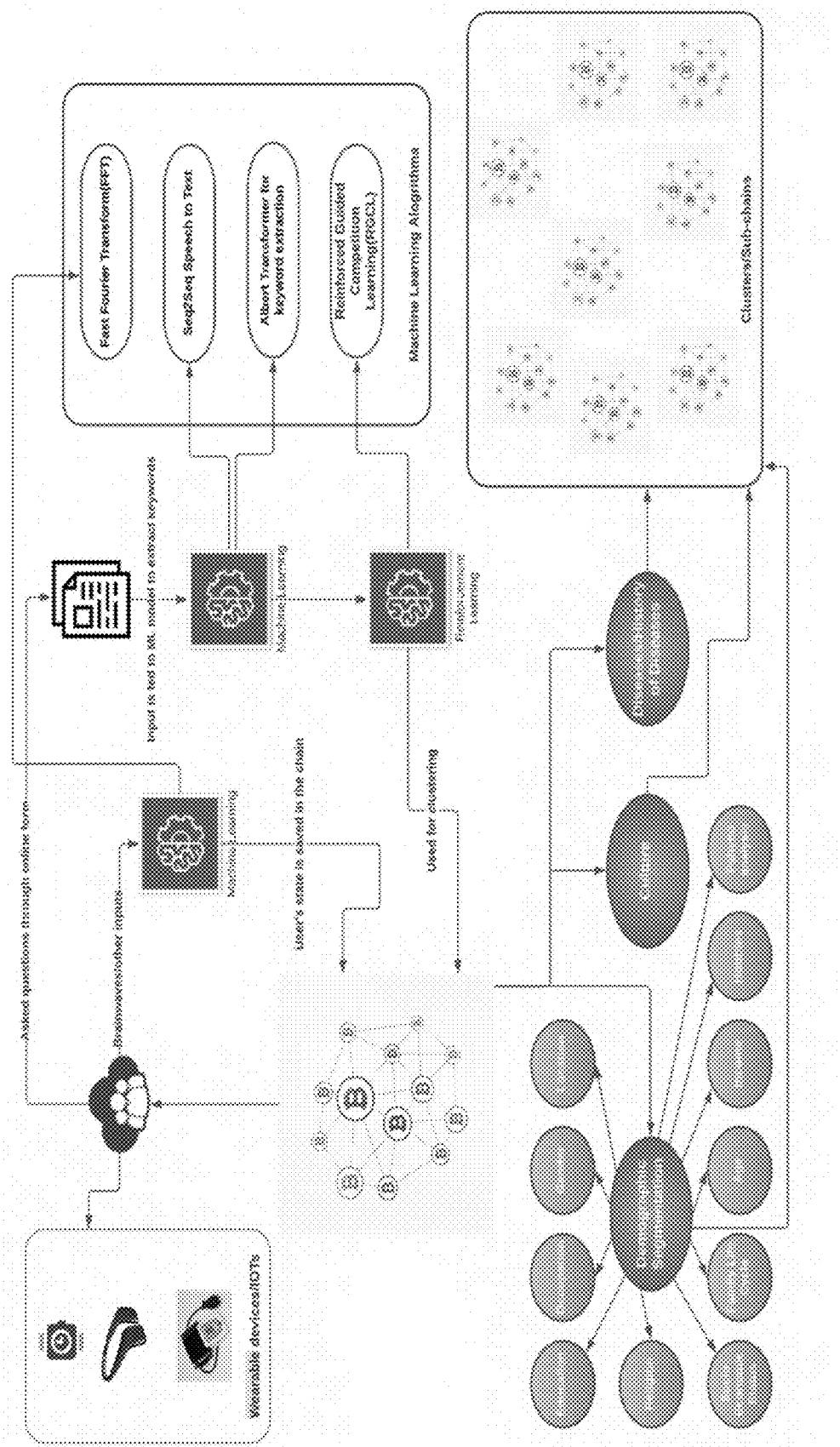

FIGS. 6A, 6B, and 6C illustrate example system data flows for use with embodiments of the present disclosure.

Figure 6D:
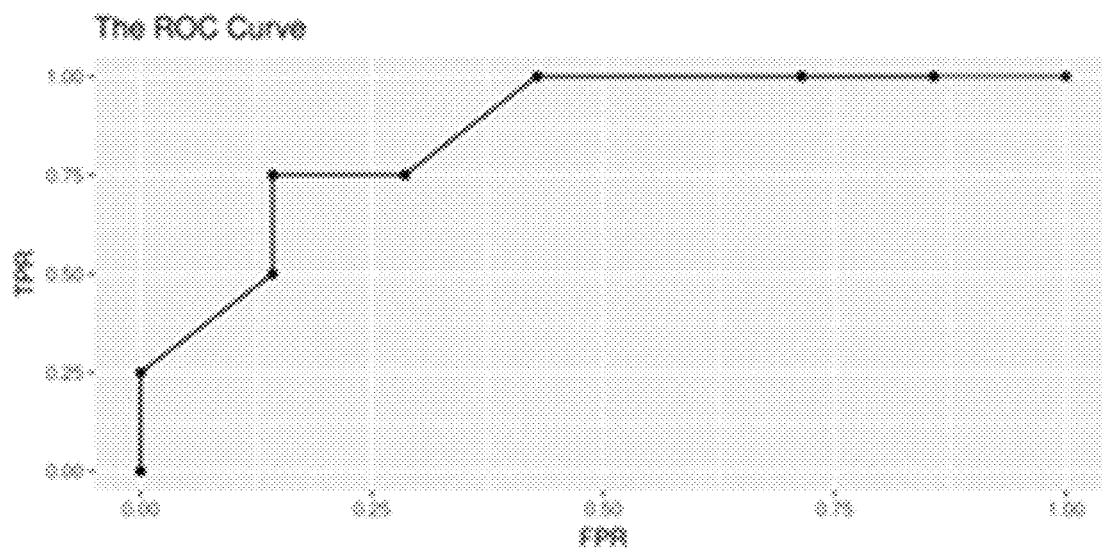

FIG. 6D illustrates an example ROC curve.

Figure 6E:
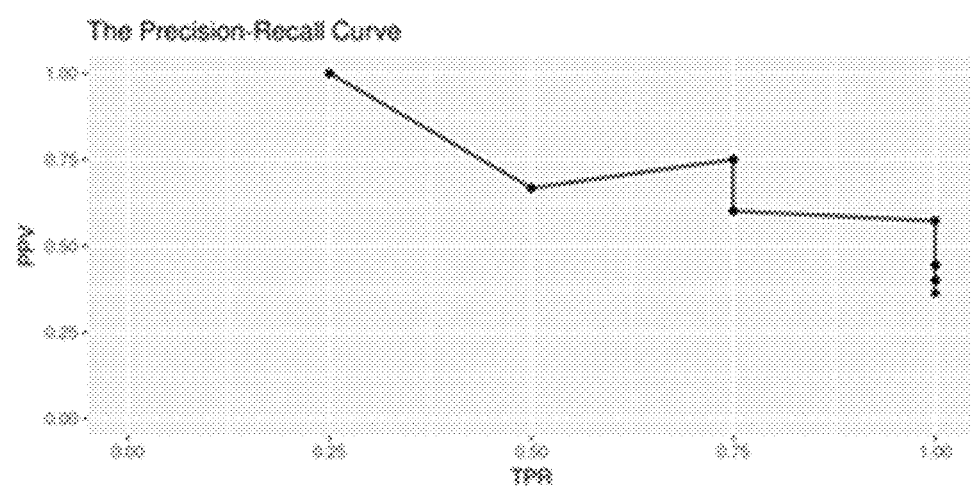

FIG. 6E illustrates an example precision-recall curve.

Figure 7:
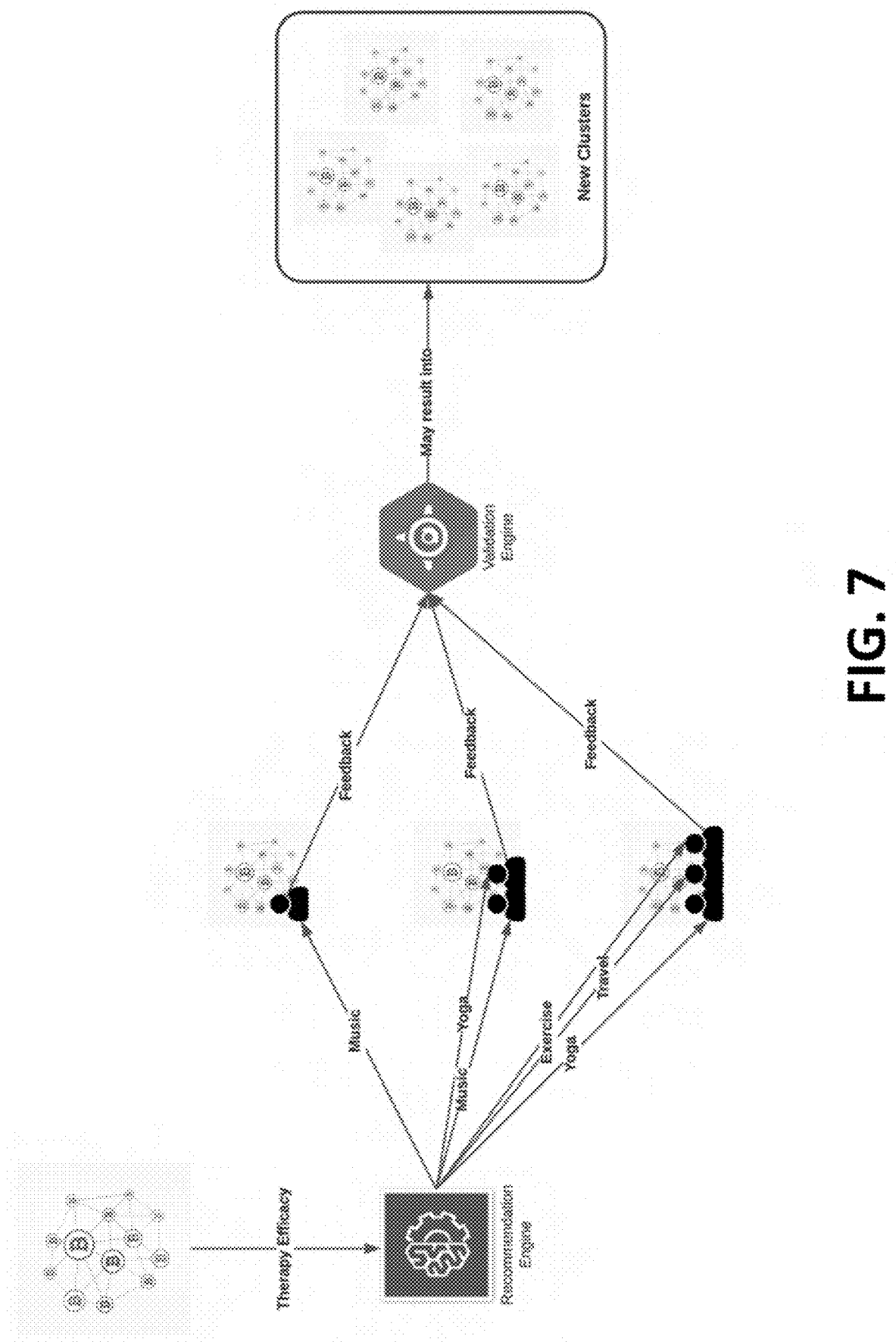

FIG. 7 illustrates an example therapy efficacy validation flow for use with embodiments of the present disclosure.

Figure 8:
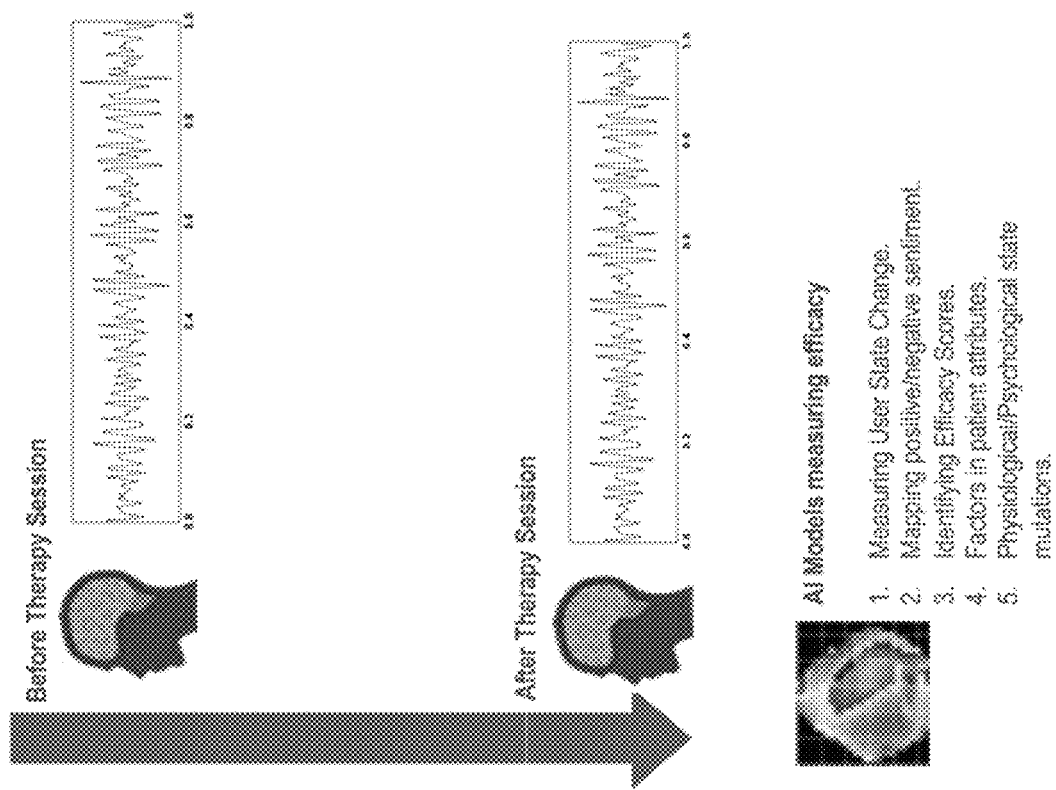

FIG. 8 illustrates an example therapy evaluation data capture for use with embodiments of the present disclosure.

Figure 9:
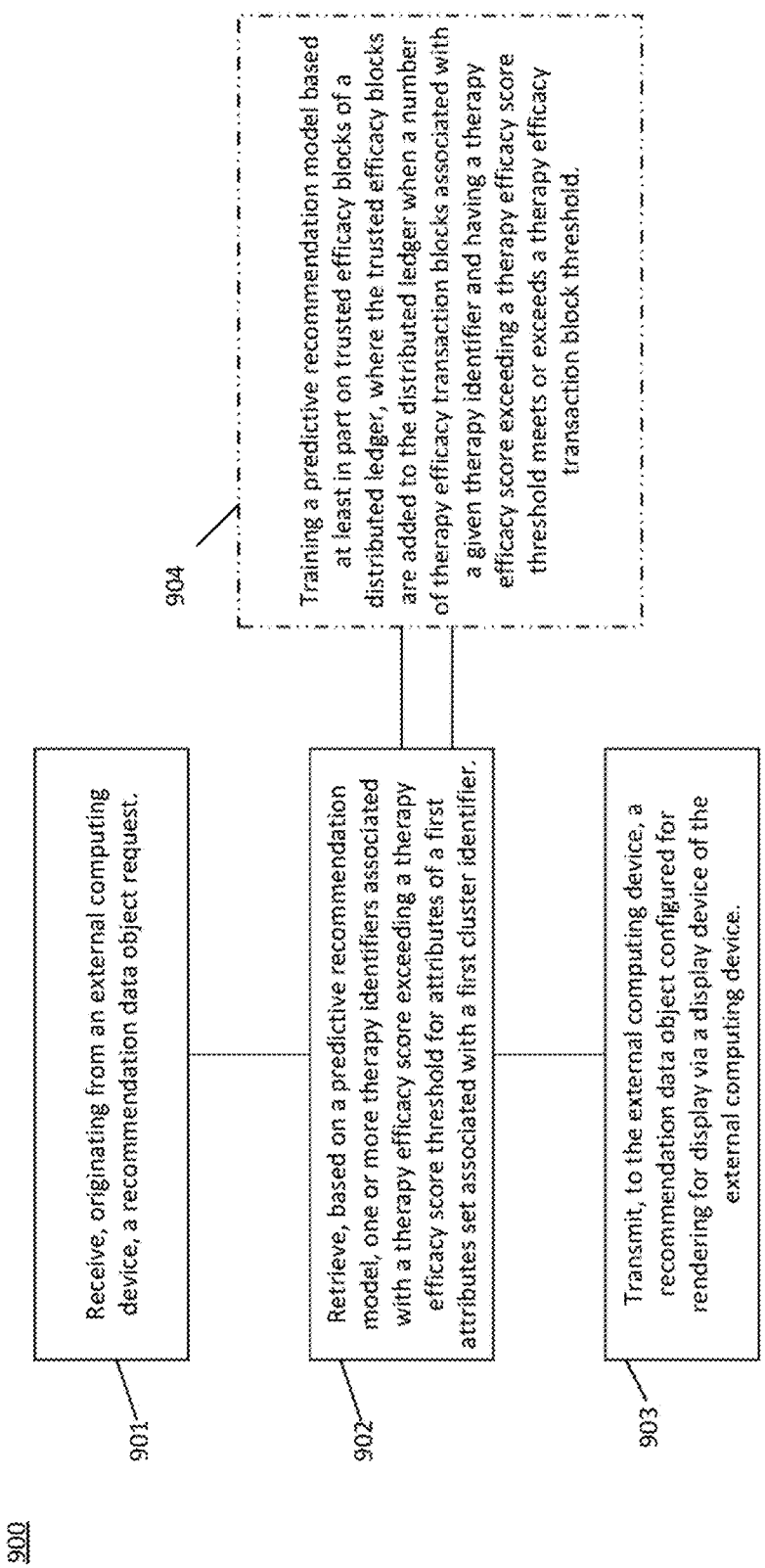

FIG. 9 illustrates an example data flow for use with embodiments of the present disclosure.

In accordance with common practice some features illustrated in the drawings cannot be drawn to scale. Accordingly, the dimensions of some features can be arbitrarily expanded or reduced for clarity. In addition, some of the drawings cannot depict all the components of a given system, method or device. Finally, like reference numerals can be used to denote like features throughout the specification and figures.

DETAILED DESCRIPTION

Various embodiments of the present disclosure now will be described more fully hereinafter with reference to the accompanying drawings, in which some, but not all embodiments of the disclosures are shown. Indeed, these disclosures may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present disclosure are described with reference to predictive and decentralized data analysis, one of ordinary skill in the art will recognize that the disclosed concepts can be used to perform other types of data analysis.

I. OVERVIEW AND TECHNICAL ADVANTAGES

Embodiments herein overcome the aforementioned challenges and more through the generation of meaningful data sets through the use of crowd sourcing and clustering in order to provide predictive recommendations. Feature vectors associated with a vast number of users utilized for training a recommendation model, and the resulting recommendation data objects are validated according to physiological observations. Only those recommendation data objects resulting in a given efficacy threshold value then receive approval for inclusion in a distributed ledger (e.g., according to a consensus mechanism). Such features of the present embodiments ensure the recommendation model is trained with an appropriate training data set (e.g., without noise introduced by less than relevant or meaningful metadata), which results in predictive recommendations that are more meaningful to a given user. Further, the present embodiments ensure that there is a statistically significant amount of data upon which decisions about recommendations may be made, and that the data remains anonymous and rigorously validated.

Various embodiments of the present disclosure disclose techniques for crowd sourcing therapy efficacy data, based on a statistically significant number of disparate users, in order to train and refine a predictive recommendation model that generates therapy recommendations for users. Crowd sourcing the therapy efficacy data enables meaningful validation of therapies that have been recommended, and decentralizing the system data through the use of a block chain or distributed ledger network provides immutability and anonymity for the recorded data and user information. That is, gathering therapy efficacy data from a plurality of disparate users for validating efficacy of any given therapy results in possibly inaccurate (e.g., altered), inconsistent data, as well as inadvertent breach of user confidentiality. By employing a block chain or distributed ledger network for embodiments herein, the present embodiments ensure large amounts of data (e.g., statistically significant data) while not compromising the integrity of the data nor user or patient confidentiality.

Moreover, embodiments of the present disclosure enable a therapy efficacy model configured to assign a therapy efficacy score to any given therapy identifier that was part of a recommendation data object for a user or a cluster of users. That is, the therapy efficacy model provides a trusted source of evaluation for therapies and how they relate to or how effective or ineffective they may be for any give set of user attributes. Without such a trusted source of evaluation, users are left to evaluate therapy efficacies based on less than meaningful metrics or metadata as mentioned above. The therapy efficacy model may be configured to identify the most important user attributes and therapy attributes for determining a therapy efficacy score and eliminate consideration of the less important attributes. In so doing, embodiments herein reduce processing power, time, and resources.

II. DEFINITIONS

As used herein, the terms "data," "content," "digital content," "digital content object," "information," and similar terms may be used interchangeably to refer to data capable of being transmitted, received, and/or stored in accordance with embodiments of the present disclosure. Thus, use of any such terms should not be taken to limit the spirit and scope of embodiments of the present disclosure. Further, where a computing device is described herein to receive data from another computing device, it will be appreciated that the data may be received directly from another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to another computing device or may be sent indirectly via one or more intermediary computing devices, such as, for example, one or more servers, relays, routers, network access points, base stations, hosts, and/or the like.

A block chain, also referred to as a blockchain or distributed ledger, refers to a growing list of data objects in the form of records, called blocks, linked together based on cryptography. Each block contains at least a cryptographic hash of the previous block, a timestamp, and transaction data. A block chain is immutable by nature. That is, a block chain is resistant to modification of its data because, once recorded (e.g., or added to the block chain or distributed ledger), the data in any given block cannot be altered retroactively without alteration of all subsequent blocks. For use as a distributed ledger, a blockchain can be managed by a peer-to-peer network collectively adhering to a protocol for inter-node communication and validating new blocks.

A blockchain is a decentralized, distributed, digital ledger consisting of records called blocks that is used to record transactions across many computers so that any involved block cannot be altered retroactively, without the alteration of all subsequent blocks. This allows the participants to verify and audit transactions independently and relatively inexpensively. A blockchain database may be managed autonomously using a peer-to-peer network and a distributed timestamping server.

Blocks or transaction blocks of a block chain hold batches of valid transactions that are hashed and encoded into, for example, a Merkle tree. Each block includes the cryptographic hash of the prior block in the blockchain, thereby linking the two. The linked blocks form a chain. This iterative process confirms the integrity of the previous block, all the way back to the initial block, which is known as the genesis block.

Every node in a decentralized system has a copy of the blockchain. Data quality is maintained by massive database replication and computational trust. No centralized "official" copy exists and no user is "trusted" more than any other. Transactions are broadcast to the network using software. Messages are delivered on a best-effort basis. Mining nodes validate transactions, add them to the block they are building, and then broadcast the completed block to other nodes.

Block chain smart contracts may refer to proposed contracts that can be partially or fully executed or enforced without human interaction. A feature of smart contracts is that they do not need a trusted third party (such as a trustee) to act as an intermediary between contracting entities—the block chain network executes the contract on its own. In various embodiments of the present disclosure, access to write user data or information by members of the block chain network may be controlled by a role based access control module that controls access based on the underlying block chain constructs of the network. An example of such underlying constructs include smart contracts (e.g., in Ethereum).

Machine learning is a subfield of computer science that gives computers the ability to learn without being explicitly programmed. Evolved from the study of pattern recognition and computational learning theory in artificial intelligence, machine learning explores the study and construction of algorithms that can learn from and make predictions on data. Such algorithms overcome following strictly static program instructions by making data-driven predictions or decisions through building a machine learning model from sample inputs. Machine learning is employed in a range of computing tasks where designing and programming explicit algorithms with good performance is difficult or infeasible.

Machine learning enables prediction-making through the use of computers. Machine learning can be unsupervised for exploratory data analysis. Machine learning can also be unsupervised and be used to learn and establish baseline behavioral profiles for various entities and then used to find meaningful anomalies. Machine learning is used to devise complex models and algorithms that lend themselves to prediction; also known as predictive analytics. These machine learning models allow researchers, data scientists, engineers, and analysts to produce reliable, repeatable decisions and results, and uncover hidden insights through learning from historical relationships and trends in the data.

The term "machine learning model" refers to a machine learning task. A machine learning model typically comprises a title and encompasses one or more target variables.

The term "target variable" refers to a value that a machine learning model is designed to predict. In the present embodiments, historical data is used to train a machine learning model to predict the target variable. Historical observations of the target variable are used for such training.

The term "machine learning model identifier" refers to one or more items of data by which a machine learning model may be identified. For example, a machine learning model identifier may comprise ASCII text, a pointer, a memory address, and the like. In embodiments, a first machine learning model may be associated with a first machine learning model identifier and a second machine learning model may be associated with a second machine learning model identifier, and the like.

It should be appreciated that the terms "programmatically expected," "infer," "inferred," or "inference" indicate machine prediction of occurrence of certain events. For example, a "programmatically expected" or "programmatically generated" likelihood is a value or number determined by machine prediction specifying whether a policy transaction will occur in a future network period.

The term "likelihood" refers to a measure of probability for occurrence of a particular event. For example, the likelihood that a policy transaction will occur may be a value associated with a specific scale. In some implementations, the machine predictions discussed above are based, at least in part, on the "likelihood" that an event will occur.

The term "recommendation data object" refers to a collection of data and instructions that represent an item or resource of the decentralized predictive recommendation system. In some embodiments, a recommendation data object represents a predictive recommendation provided by a predictive recommendation model for a particular user identifier. A recommendation data object may comprise a user identifier and a therapy identifier associated with a therapy recommended for the user identifier.

The term "recommendation data object request" refers to one or more electronic signals representative of a request, originating from an external computing device, for one or more recommendation data objects. A recommendation data object request may be generated in response to electronic interactions by a user with the external computing device.

The terms "user," "patient," "member," or "recommender" should be understood to refer to an individual, group of individuals, business, organization, and the like; the users referred to herein are accessing a decentralized predictive recommendation system using external computing devices.

The terms "user profile," "user account," "patient profile," and "user account details" refer to information associated with a user of a decentralized predictive recommendation system, including, for example, a user identifier, biometrics data, demographic data, socioeconomic data, user attributes, and the like. The user account details can include a subset designation of user credentials, such as, for example, login information for the user including the user's username and password.

As used herein, the term "user identifier" refers to one or more items of data by which a user and this user's corresponding user account may be uniquely identified within a decentralized predictive recommendation system. For example, a user identifier may comprise ASCII text, a pointer, a memory address, and the like.

The term "therapy" refers to an attempted remediation of a health or life problem. A therapy may also be referred to as a treatment, care, or recommended course of care.

The term "therapy identifier" refers to one or more items of data by which a therapy may be uniquely identified. For example, a therapy identifier may comprise ASCII text, a pointer, a memory address, and the like.

The terms "user attribute," "attribute," "user attribute data object," or "attribute data object" refer to items of information associated with a specific to a given user, such as demographic information, environmental information, and the like. Examples of user attributes may include demographic information (e.g., age, gender, gender identity, location), environmental factor information (e.g., cultural, social, economic conditions), personality or psychological information (e.g., personality preferences provided via one or more modes such as a personality questionnaire, psychoanalysis tests, and other psychiatric methods), medical information (e.g., existing medical conditions, known allergies, dietary preferences, medical history), and the like.

The term "predictive recommendation model" refers to one or more machine learning models generated to produce recommendation data objects based on received user data objects. The predictive recommendation model may be initially trained using known therapy efficacy data associated with clusters of users, and may be continuously retrained and refined using trusted efficacy blocks generated based on a therapy efficacy model, additional therapy feedback data, and data blocks resulting from a consensus mechanism of a block chain or distributed ledger network.

The term "therapy efficacy score" refers to a programmatically generated measure of efficacy associated with a given therapy identifier for one or more users associated with a given set of attributes.

The term "therapy efficacy score threshold" refers to a magnitude or level of a therapy efficacy score associated with a given therapy identifier that is required or preferred for a therapy associated with the given therapy identifier to be considered effective for one or more users associated with a given set of attributes.

The term "attributes set" refers to a data structure comprising a plurality of attributes represented as data records.

The term "cluster" refers to a group of objects (e.g., user profile objects or transaction blocks) sharing a specific set of attributes. A cluster may be generated according to a clustering model.

The term "cluster identifier" refers to one or more items of data by which a cluster may be uniquely identified. For example, a cluster identifier may comprise ASCII text, a pointer, a memory address, and the like.

The term "trusted efficacy block" refers to a block chain or distributed ledger block generated based on one or more therapy efficacy transaction blocks, when (1) the one or more therapy efficacy transaction blocks are associated with a common therapy identifier, (2) a therapy efficacy score of the one or more therapy efficacy transaction blocks meets or exceeds a therapy efficacy score threshold, and (3) a number or count of the one or more therapy efficacy transaction blocks meets or exceeds a therapy efficacy transaction block threshold. In certain embodiments, trusted efficacy blocks are generated according to a consensus mechanism. The trusted efficacy block may represent a latest status with respect to an efficacy of the therapy associated with the therapy identifier for a given set of user attributes. The trusted efficacy blocks may further be used to re-train or refine a predictive recommendation model for providing recommendations of therapies to users.

The term "therapy efficacy transaction block threshold" refers to a number or count of therapy efficacy transaction blocks having a therapy efficacy score associated with a given therapy identifier, where the therapy efficacy score for each of the therapy efficacy transaction blocks meets or exceeds a therapy efficacy score threshold, required or preferred for a trusted efficacy block to be generated and added to a block chain or distributed ledger network.

The term "feature vector" refers to an n-dimensional vector (e.g., data structure) including digital features representing an object. The feature vector may include a number of data records, each associated with a feature or attribute of the object.

The term "clustering model" refers to a machine learning or statistical analysis task involving grouping a set of objects in a way such that objects in the same group (e.g., a cluster) are more similar to each other than to those in other groups (e.g., other clusters).

The terms "biometrics transaction block" or "patient profile transaction block" refer to block chain transaction blocks generated based on one or more of patient profile information provided from a user (e.g., by way of an external computing device) or biometrics data provided by a user (e.g., by way of an external computing device or other electronic sensor mechanism).

The term "therapy feedback object" refers to one or more items of data representative of electronic signals received indicative of feedback related to a given therapy associated with a therapy identifier. Accordingly, a therapy feedback object may include a therapy identifier as well as one or more data records (e.g., therapy feedback data records) each associated with a different item of feedback.

The terms "historical patient profile data" or "historical patient data" or "historical user data" to refer to user data previously collected and stored in association with a given user identifier.

The term "known therapy efficacy data" refers to therapy efficacy data associated with a given therapy previously collected and stored in association with a given therapy identifier.

The term "recommendation category" refers to a grouping or label associated with a therapy contained within a recommendation data object. Examples of a recommendation category include lifestyle recommendation, mindfulness activity, sleep pattern, exercise regime, workout strategy, behavioral guideline, daily routine adjustment.

The term "recommender category" refers to a grouping or label associated with a recommender associated with a therapy identifier. Examples of a recommender category include psychiatrist, behavioral therapist, researcher, educational institute, wellness coach, lifestyle guru, life coach.

The term "similarity score" refers to a programmatically generated measure of similarity between two objects.

The term "sub-chain" refers to a fork in a block chain or distributed ledger network involving one or more clusters or users. A sub-chain may be created, in certain embodiments, to enable communication between and information sharing by users within a cluster based on similarities they share.

The term "similarity score threshold" refers to a magnitude or level of a similarity score associated with creating a sub-chain of clusters. For example, when two or more clusters have a similarity score meeting or exceeding a similarity score threshold—that is, the two or more clusters meet a level of similarity to one another—a sub-chain containing those clusters may be added to a block chain or distributed ledger network.

The term "electronic sensor" refers to a device, module, machine, or subsystem whose purpose is to detect events or changes in its environment and send the information to other devices. Examples of electronic sensors include wearable sensors, smart watches, fitness devices, audio recording devices, video recording devices, biometric sensors, throat patches, EEG sensors, galvanic skin reaction sensors, sweat sensors, or blood pressure sensors.

The terms "biometric data" and "physiological data" refers to electronic items representative of body measurements and calculations related to human characteristics.

The terms "historical patient biometric data" or "historical biometric data" refer to biometric data previously collected and stored in association with a given user identifier.

The term "psychological data" refers to electronic items representative of experiences or behaviors of users.

The term "control group object" refers to a data object utilized in an evaluation designed to minimize the effects of less important attributes of feature vectors associated with users and therapy efficacies. For example, based in part on a predictive recommendation model, a therapy efficacy model, and trusted efficacy blocks, a group of user objects may be identified as the best candidates for certain recommendation data objects.

II. COMPUTER PROGRAM PRODUCTS, METHODS, AND COMPUTING ENTITIES

Embodiments of the present disclosure may be implemented in various ways, including as computer program products that comprise articles of manufacture. Such computer program products may include one or more software components including, for example, software objects, methods, data objects, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 is a schematic diagram of an example system architecture 100 for performing predictive recommendation steps/operations and generating corresponding user interface data (e.g., for providing and/or updating a user interface). The system architecture 100 includes a predictive recommendation system 101 comprising a predictive recommendation computing entity 106 configured to generate predictive recommendation data objects as well as maintaining of a predictive recommendation model and a therapy efficacy model. The predictive recommendation system 101 may communicate with one or more external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The system architecture 100 includes a storage subsystem 108 (e.g., a repository) configured to store at least a portion of the data utilized by the predictive recommendation system 101. The predictive recommendation computing entity 106 may be in communication with one or more external computing entities 102. The predictive recommendation computing entity 106 may be configured to receive requests and/or data from external computing entities 102, process the requests and/or data to generate predictive outputs (e.g., recommendation data objects), and provide the predictive outputs to the external computing entities 102. The external computing entity 102 may periodically update/provide raw input data (e.g., data objects describing patient profile or biometric data) to the predictive recommendation system 101.

The storage subsystem 108 may be configured to store at least a portion of the data utilized by the predictive recommendation computing entity 106 to perform predictive recommendation steps/operations and tasks. The storage subsystem 108 may be configured to store at least a portion of operational data and/or operational configuration data including operational instructions and parameters utilized by the predictive recommendation computing entity 106 to perform predictive recommendation steps/operations in response to requests. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

A. Exemplary Predictive Recommendation Computing Entity

FIG. 2 provides a schematic of a predictive recommendation computing entity 106 according to one embodiment of the present disclosure. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive recommendation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive recommendation computing entity 106 may include, or be in communication with, a processing element 205 (also referred to as processors, processing circuitry, and/or similar terms used herein interchangeably) that communicate with other elements within the predictive recommendation computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the predictive recommendation computing entity 106 may further include, or be in communication with, non-volatile media (also referred to as non-volatile storage, memory, memory storage, memory circuitry and/or similar terms used herein interchangeably). In one embodiment, the non-volatile storage or memory may include non-volatile memory 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive recommendation computing entity 106 may further include, or be in communication with, volatile media (also referred to as volatile storage, memory, memory storage, memory circuitry and/or similar terms used herein interchangeably). In one embodiment, the volatile storage or memory may also include volatile memory 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive recommendation computing entity 106 with the assistance of the processing element 205 and operating system.

As indicated, in one embodiment, the predictive recommendation computing entity 106 may also include a communications interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive recommendation computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive recommendation computing entity 106 may include, or be in communication with, one or more input elements, such as a keyboard input, a mouse input, a touch screen/display input, motion input, movement input, audio input, pointing device input, joystick input, keypad input, and/or the like. The predictive recommendation computing entity 106 may also include, or be in communication with, one or more output elements (not shown), such as audio output, video output, screen/display output, motion output, movement output, and/or the like.

B. Exemplary External Computing Entity

FIG. 3 provides an illustrative schematic representative of an external computing entity 102 that can be used in conjunction with embodiments of the present disclosure. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to predictive recommendation computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive recommendation computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive recommendation computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive recommendation computing entity 106 and/or various other computing entities.

In another embodiment, the external computing entity 102 may include one or more components or functionality that are the same or similar to those of the predictive recommendation computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. EXEMPLARY SYSTEM OPERATIONS

Embodiments herein employ one or more networks of block chain, including one or more private block chain or one or more public block chains. The network(s) can further also include one or more hybrid blockchain with some responsibilities and participants private while others public. The block chain allows one or more parties to be part of the network in one or more limited capacities. The participants may include one or more roles including the participants receiving the lifestyle recommendations, participants emitting the recommendations feedback, participants validating the results, participants offering one or more recommendations. Further, the participants may further include other administrative roles like the cluster operation, the noise filters, and the like.

One or more set of participating members can provide one or more lifestyle recommendations. Each recommendation may also include one or more additional identifiers for a targeted audience. Example of a lifestyle recommendation includes performing 30 minutes of high intensity workout in the morning along with following Keto's diet for weight loss. Example additional identifiers for the target audience include users within the age group of 30 to 50 with no prior cardiac conditions. The participating members providing recommendations may include an individual or an entity such as an organization, a research group, and the like.

One or more machine learning/ledger admin modules use one or more machine learning algorithms to identify clusters of users on which the lifestyle recommendations may be applicable. The machine learning/ledger admin modules may identify one or more clusters of participating members.

The machine learning/ledger admin modules can rely on the additional recommendation attributes provided along with the recommendation for demographic clustering. Additionally, the machine learning/ledger admin modules may further use additional techniques for randomly identifying target demographic clusters based on defined rules and policies, along with risk assessment as control groups.

An example of an identified cluster group for a recommendation practice includes users matching the demographic criteria of the recommendation like age, gender, culture, existing conditions, and the like. Examples of a random controlled cluster group includes users within different age buckets that do not have existing chronic medical conditions.

One or more participant members of the identified recommendation cluster initiates request to become part of the block chain or distributed ledger network. The participants members upon the inclusion can apply one or more recommendations provided as part of the cluster for lifestyle changes.

The participating members additionally configure one or more biometric devices, wearable sensors and smart devices like smart watches, EEG headbands, sensors, blood pressure sensors, Apple Watch, and the like. These devices provide one or more mechanisms to monitor the efficacy of the lifestyle recommendations in real-time.

Device data from one or more biometric sensors and other wearable devices are streamed to the block chain or distributed ledger network from each participating member. This includes but is not limited to all the sensor data that provide information on the time of pursuing the recommendations, provides mechanisms on measuring the efficacy of the routine, the changes in the physiological and psychological areas of the participating members.

One or more participating machine learning/ledger admin modules use one or more machine learning algorithms to derive the efficacy of the recommendation on one or more set of participating members. The process uses the raw biometric sensors and device data sent from the participating members to the chain. Example of the deduction of the efficacy of the recommendations includes a percentage of users from the control groups who saw positive results with configurable percentage of positive change. The deductions may further vary to derive efficacy in various dimensions of participants from one or more cluster. The process further includes standards techniques of removing the noise. Example of noise includes participating members who did not follow the recommendations, those who provide wrong measurement, and the like.

One or more participating machine learning/ledger admin modules use the quantifiable efficacy results as predicted using the ML processes herein to expand the block chain or distributed ledger network using the recommendations overall efficacy. The recommendation efficacy includes one or more quantifiable metrics for the success factor of the recommendations on a given controlled group. Examples of such includes the above example recommendation proves to be 80% effective on the example cluster group identified.

The efficacies identified from each active participant is captured and the consensus is made using a novel consensus protocol that uses major voting mechanism. The major voting consensus protocol derives the agreed therapy efficacy for an entire group. If more than 51% of users using the therapy shows positive results, the block is expanded.

Efficacy validation herein ensures that none of the participating members can provide inaccurate assessments intentionally. The machine learning/ledger admin modules use the consensus approach of block chain to derive the recommendation ratings using a P2P fashion from number of nodes to derive the recommendation ratings.

One or more leaderboards may be created by the chain to describe one or more top recommendations for one or more participating members. Each participating member may get one or more recommendations based on the members demographics, and other identifiable medical and behavioral conditions. This includes but not limited to existing medical conditions, behavioral conditions, demographic, social economic conditions.

Figure 4A:
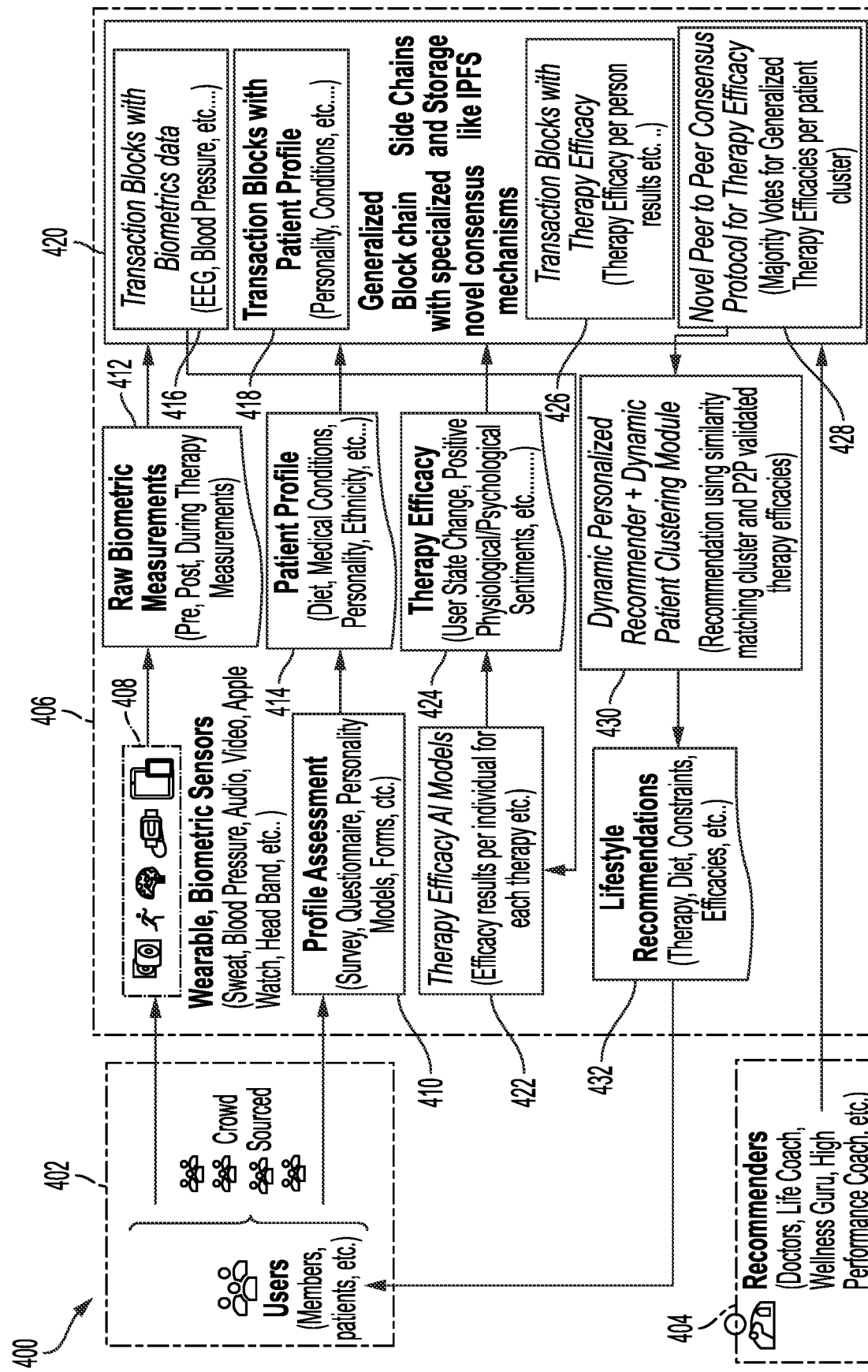
Figure 4B:
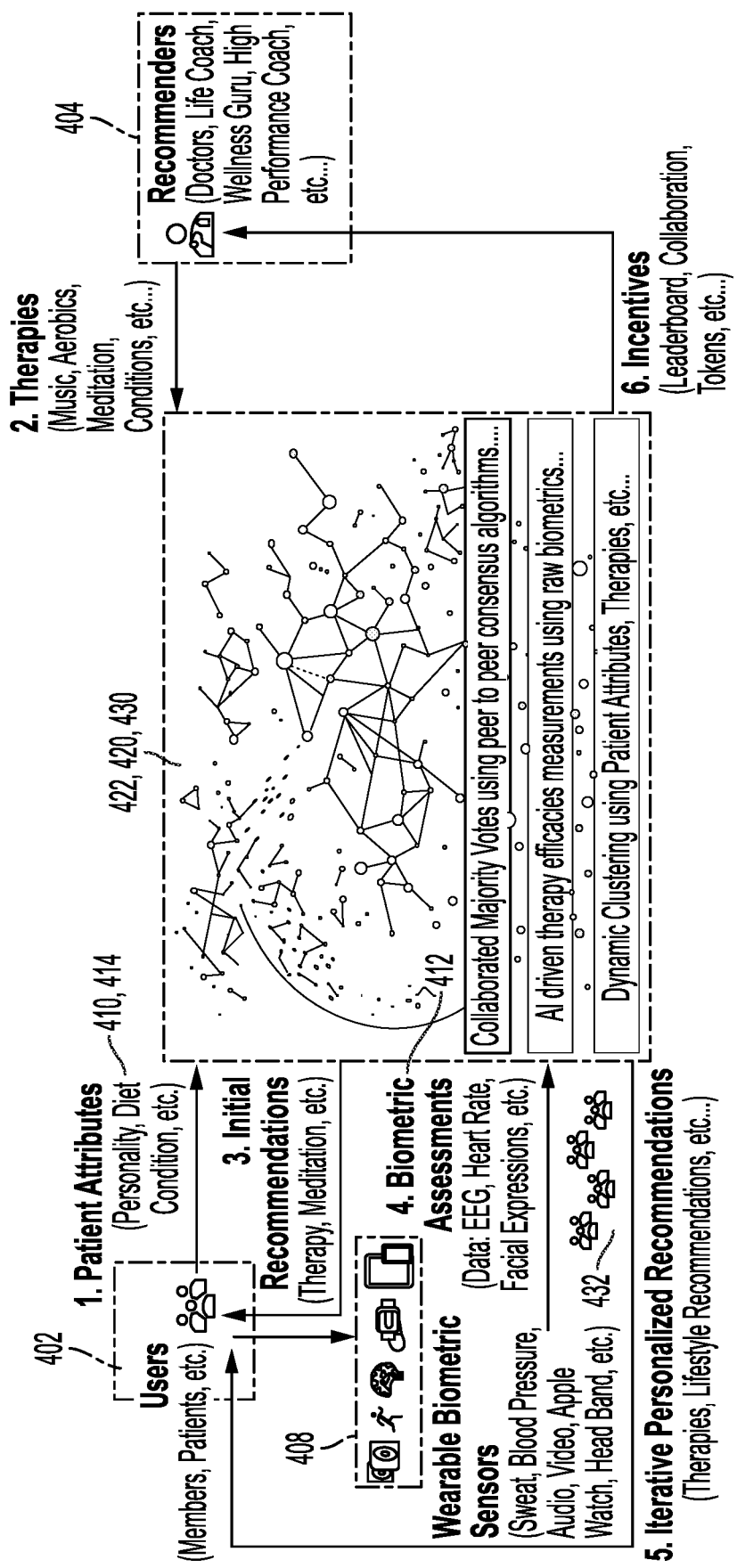
Figure 4C:
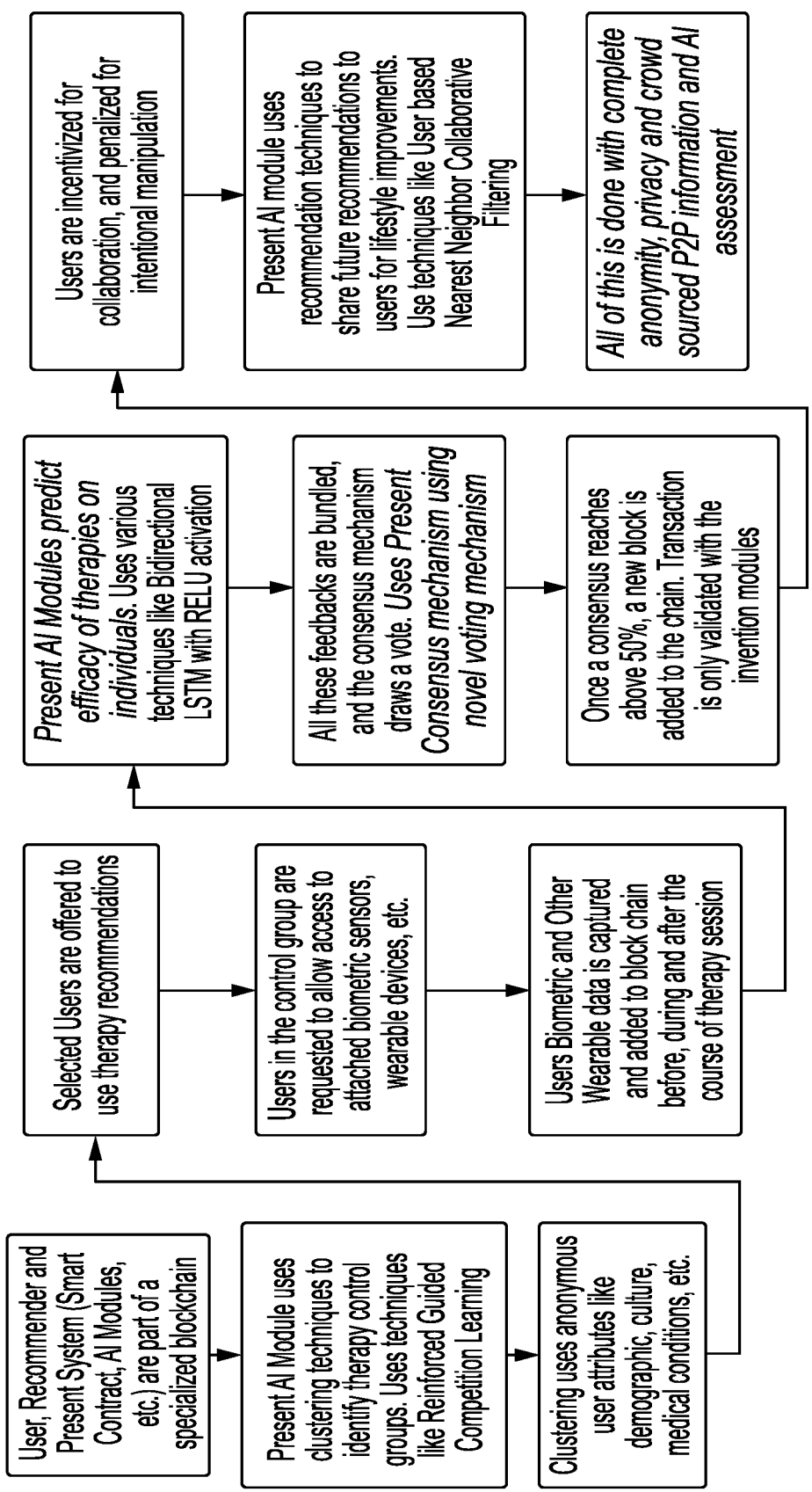
Figure 4D:
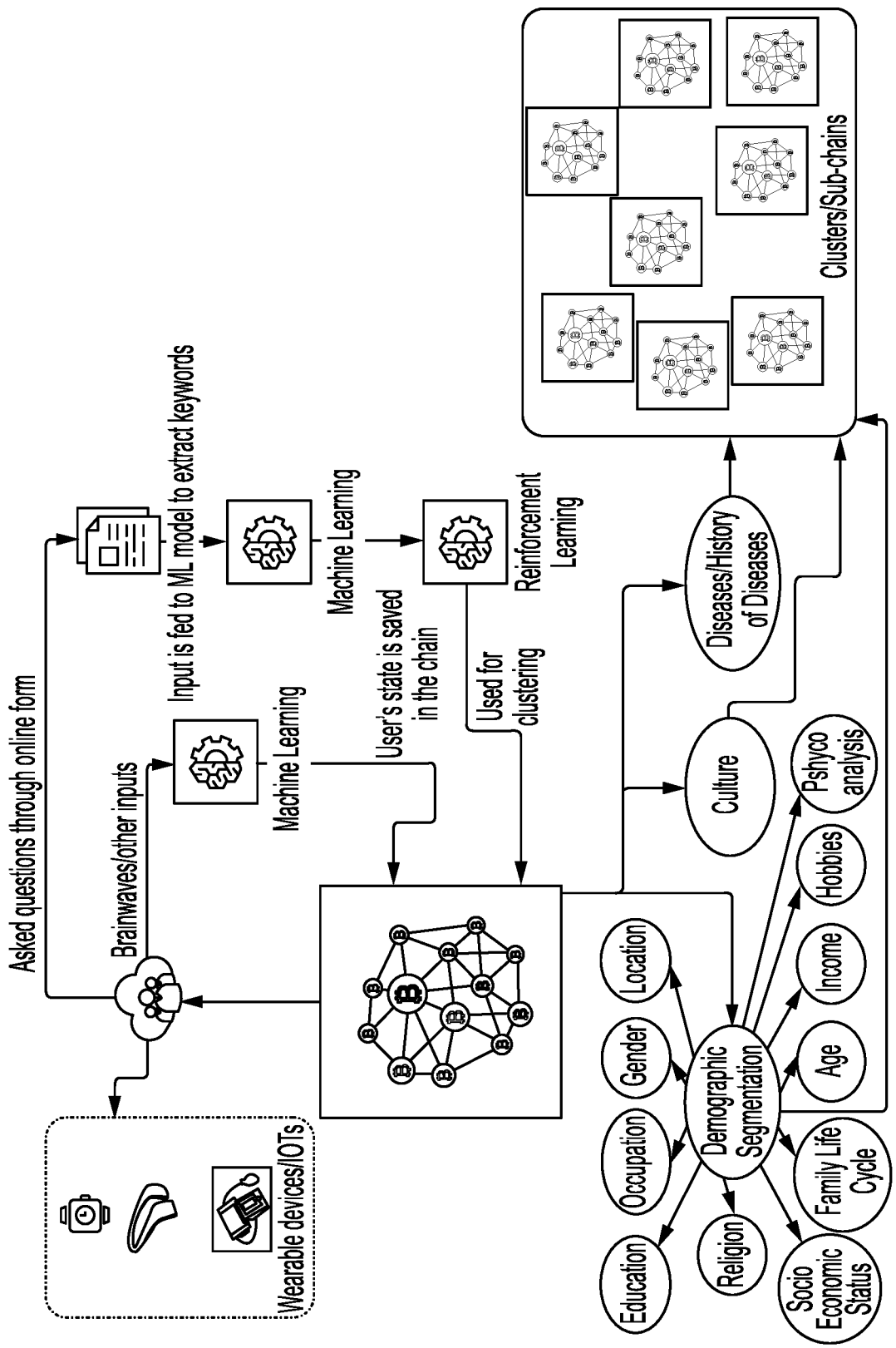

FIGS. 4A, 4B, 4C, and 4D illustrate an example system data flow 400 for use with embodiments of the present disclosure. In FIGS. 4A and 4B, a plurality of users 402 (e.g., by way of client or external computing devices), and a plurality of recommenders 404 (e.g., by way of client or external computing devices), may electronically (e.g., by way of a communications network) interact with a predictive recommendation system 406 (e.g., such as predictive recommendation system 101). The predictive recommendation system 406 may receive as input signals from the plurality of users 402 sensor data 408 (e.g., sweat levels, blood pressure, audio signals, video signals, other available sensor data; e.g., via wearable, biometric sensors or via smart phones), and profile information 410 including user attributes (e.g., by way of interactions with a user interface and including answers to surveys, questionnaires, personality models, or generally forms). Supplemental to the sensor data 408, raw biometric assessments 412 (e.g., biometric and other measurements) may be collected before, during, and after implementation of a recommendation by a given user. A user or patient profile 414 may be generated based on the profile information 410 and any other information obtained from or about the user or patient.

Based on the obtained biometric data (e.g., 408, 412), biometrics transaction blocks 416 may be generated and added to a distributed ledger 420 (e.g., blockchain) for a given user. Similarly, based on the obtained patient profile data (e.g., 410, 414), patient profile transaction blocks 418 may be generated and added to the distributed ledger 420 for the given user. The biometrics transaction blocks 416 may resemble, in certain embodiments, electronic transactions including data objects having a plurality of records, where each record represents an attribute associated with a given user's biometric measurements. Similarly, the patient profile transaction blocks 418 may resemble, in certain embodiments, electronic transactions including data objects having a plurality of records, where each record represents an attribute associated with the given user's patient profile data. The patient profile transaction blocks 418 and the biometrics transaction blocks 416 may be added to the distributed ledger 420 based on validating a hash of the blocks and then expanding the distributed ledger 420 (e.g., the chain) with the new blocks.

A therapy efficacy model 422 may be trained using historical patient profile and biometric data as well as known efficacy results, and may be continuously updated or re-trained according to updated transaction blocks 416, 418 and therapy efficacy data 424. When updated efficacy results are available for any given user, based upon recommendations provided to the user and recorded efficacy data 424 associated with how well the recommendations have worked for the given user, therapy efficacy transaction blocks 426 may be generated and added to the distributed ledger 426. The therapy efficacy transaction blocks 426 may resemble, in certain embodiments, electronic transactions including data objects having a plurality of records, where each record represents an attribute associated with the given user's efficacy data (e.g., user state change, positive physiological or psychological sentiments, and the like). That is, the therapy efficacy model 422 may use one or more machine learning models to identify the efficacies of one or more therapies or recommendations provided to one or more users. The efficacies measurements are performed and recorded per individual patient. Each patient's therapy efficacies results are stored in the blockchain as therapy efficacy transaction blocks 426.

In embodiments, each therapy efficacy transaction block 426 may be associated with an efficacy identification object representative of a therapy recommendation the efficacy of which is evaluated and indicated as a record within the therapy efficacy transaction block 426. In certain embodiments, the efficacy indication object may be a binary value indicative of a yes (e.g., 1) or a no (e.g., 0). An efficacy indication object having a value of 1 or yes may be representative of an outcome associated with a given therapy recommendation having been "effective" for a given user for the specific therapy efficacy transaction block 426.

In embodiments, an efficacy consensus protocol 428 evaluates all of the therapy efficacy transaction blocks 426 of the distributed ledger 420 and, once a number of therapy efficacy transaction blocks for a given efficacy identification object (e.g., a specific therapy or therapy recommendation) reaches an efficacy threshold value (e.g., a majority, greater than 50%, or the like), a trusted efficacy block may be generated and added to the distributed ledger 420 for the given efficacy identification object. The trusted efficacy block may represent a latest state of efficacy for the given efficacy identification object (e.g., the specific therapy or therapy recommendation).

In embodiments, an example efficacy consensus protocol 428 may utilize standard blockchain constructs to validate a hash of the efficacy transaction block and expand the distributed ledger (e.g., the chain) with the new blocks. The efficacy consensus protocol 428, by using a majority "votes" associated with the efficacy of a given efficacy identification object (e.g., the recommended therapies) enables the creation of a single transaction efficacy measurement. This might include but not limited to the quantifiable efficacy of the therapy, the therapy identifiers, the dynamic clustered participants, demographics, and other metrics to offer new recommendations. This can be achieved but not limited to by using smart contracts in existing blockchain ecosystems.

In embodiments, a dynamic clustering module 430 uses one or more machine learning algorithms or models to identify one or more sets of users from the plurality of users 402 to be part of a control group to which one or more recommendations and therapies (e.g., therapy efficacy objects) 432 can be suggested (e.g., presented, by way of rendering a user interface on an external computing device). An example of such includes identifying a subset of participating users from all the active users on the chain, based on attributes (e.g., feature vector records, as discussed herein) associated with the users, that might be applicable for a recommendation.

FIG. 5 illustrates an example block chain or distributed ledger network 500 for use with embodiments of the present disclosure. In FIG. 5, participants in the example block chain network 500 may include a plurality of users 501A, 501B, 503C, 501N, as well as one or more recommenders (e.g., by way of an external computing device) 502, and an ML node 503. In various embodiments, users 501A-501N only have the ability to add their data onto the network 500 and may be restricted from reading other users' data. The users 501A-501N can access recommended therapies (e.g., recommendation data objects or predictive recommendation data objects) provided to their associated computing devices by way of the ML node 503. In various embodiments, recommenders 502 (e.g., by way of an external computing device) provide as input to the network 500 one or more lifestyle or other recommendations for one or more types of target audiences or users. In various embodiments, the ML node 503 is the only node with read access to any data provided to the network 500. The ML node 503 executes one or more machine learning models to provide predictive recommendations as discussed herein.

In various embodiments, each of the plurality of users 501A-501N may actively register themselves to be members or participants in the block chain or distributed ledger network 500. It will be appreciated that the block chain or distributed ledger network 500 ensures, using underlying block chain constructs, that private information associated with the users 501A-501N is securely saved with anonymity.

Registering with the block chain or distributed ledger network 500 for a user of the plurality of users 501A-501N may involve the user providing user profile and other data that is securely saved to the network 500. The information may include, for example, demographic information (e.g., age, gender, gender identity, location), environmental factor information (e.g., cultural, social, economic conditions), personality or psychological information (e.g., personality preferences provided via one or more modes such as a personality questionnaire, psychoanalysis tests, and other psychiatric methods), medical information (e.g., existing medical conditions, known allergies, dietary preferences, medical history), and the like.

Registering with the block chain or distributed ledger network 500 for a member of the one or more recommenders 502 may involve the recommender providing one or more lifestyle or other recommendations for one or more target audiences. The recommender information and other data is securely saved to the network 500 with anonymity. Recommendations may include, for example, music therapy, exercise styles, dietary habits, and more.

FIGS. 6A, 6B, and 6C illustrate example data flows for use with embodiments of the present disclosure. In FIG. 6A, a plurality of clusters 601A, 601B, . . . , 601N are generated, for example, based on reinforcement learning (e.g., unsupervised) associated with feature vectors generated for each user of a plurality of users of the example network (e.g., 500). The feature vectors are data object comprising a plurality of records, where each record corresponds to an item of data associated with a user. The item of data can be an attribute, a value associated with an answer to a survey or profile questionnaire, and the like. For example, a feature vector for a given user may include records each containing the following information:

| i. | Age-31 |
|---|---|
| ii. | Gender-F |
| iii. | Location-CA |
| iv. | Occupation-Doctor (MBBS) |
| v. | Income-100,000$ |
| vi. | Hobbies-Trekking, Movies |
| vii. | Socio-economic status-middle |
| viii. | Education-Masters in Medicinal Science |
| ix. | Culture-Urban fast life |
| x. | Any existing or historical health issue or disease-High blood pressure |

The clusters (e.g., 601A, 601B, 601N) each contain feature vectors of users (e.g., 602A, 602B, . . . 602N) having similar traits or attributes. Using supervised learning and based on receiving validation data associated with therapy recommendations (e.g., 603A-N), the clusters may be more refined (e.g., see FIG. 7).

In various embodiments, the feature vectors for the users are generated based on answers provided by way of an electronic questionnaire (e.g., the users may provide the answers by way of interactions with an electronic interface via text or speech). In embodiments employing input received from users by way of speech, speech-to-text machine learning may be utilized to convert the received audio signals into text for use in further processing. Keyword extraction based machine learning may also be utilized in various embodiments for generating targeted keywords based on received audio or text signals and the targeted keywords may be utilized in the aforementioned reinforcement learning. Examples of processing received inputs are depicted in FIGS. 6B, 6C.

A non-limiting example of reinforcement learning for use with embodiments of the present disclosure includes Reinforced Guided Competition Learning (RGCL), which is a reinforcement-based adaptation of Learning Vector Quantization (LCV), to segregate users into clusters based on their inputs as described above.

Recommendation data objects may be generated and presented (e.g., configured for rendering via a display device of a computing device and transmitted to the computing device) to users according to methods described herein. The recommendation data objects may comprise digital content representative of one or more recommendations 603A-N for a user of the computing device to implement.

With reference to FIG. 6B, recommendation data objects 653 may be generated according to a predictive recommendation model 654 employing nearest neighbor collaborative filtering and Jaccard similarity (e.g., a measurement to check similarity over differences; also known as intersection over union) to select the best recommendation based on which therapies (e.g., recommendations) worked best for similar users.

Continuing with reference to FIG. 6B, in order to measure the efficacy of any given recommendation 653 or therapy (e.g., by way of a validation engine or therapy efficacy model 652) recommended to users by embodiments of a recommendation engine or predictive recommendation model 654 herein, the present embodiments employ a plurality of metrics based on feedback 651 received from users who were recommended and tried the given recommendation or therapy. Examples of such metrics include RMSE, accuracy, ROC curve, precision, recall, and precision recall curve.

When a user is saving a given set of statistics or information associated with a therapy recommendation, a data object (e.g., 604A, 604B, 604C, 604N) may be generated containing the information (e.g., cluster identifier, user state objects, therapy identifier, feedback object(s)). Feedback object(s) may include biometric data captured using sensors or devices such as EEG headbands, smart watches, blood pressure sensors, sweat sensors, galvanic skin reaction sensors, Apple watch, other smart watch, and the like. A user state object may be generated based on the feedback information such that a classification is assigned as a user state. Examples of a user state may include happy, fear, surprised, sad, neutral. The data objects 604A, 604B, 604C, 604N may be added to the distributed ledger or block chain network 500 by way of smart contracts (e.g., 605A, 605B, 605C, 605N) or other mechanism for adding to the chain 500. A consensus mechanism 606 as described herein may, upon receiving a majority or threshold number of smart contracts associated with a given therapy identifier that indicate a positive efficacy, generate a new block 607 indicative of the therapy identifier having positive efficacy and being a candidate for recommendations.

Continuing with reference to FIG. 6B, in various embodiments, a plurality of sub-chains 656A-656N may be generated to enable interactions and information sharing between similar users within the network 500. This may be accomplished via clustering of users according to similarity scores.

An example json illustrating a user's state is included below:

```
{
"happy": 0.73,
"sad": 0.05,
"surprised": 0.01,
"fear": 0.002,
"neutral": 0.2
}
```

As an example (e.g., see FIG. 8), consider an initial recommendation is provided to the user, whose state is illustrated above, to listen to a music (a certain genre to give targeted therapy). A subsequent user state may be shown below:

```
{
"happy": 0.83,
"sad": 0.02,
"surprised": 0.01,
"fear": 0.002,
"neutral": 0.1
}
```

The user may also be asked to provide feedback whether the recommendation (e.g., the targeted therapy) worked or not. Based on the feedback, a confusion matrix can be generated based on multiple sets of feedback received (e.g., including from other users). Accordingly, the following examples of performance metrics may be used to measure an effectiveness of the recommendations.

FIG. 6D illustrates an example ROC curve. Receiver operating characteristic (ROC) curves may be used for evaluating the predictive performance of scoring classifiers. In ROC curves, the true positive rate (TPR, y-axis) is plotted against the false positive rate (FPR, x-axis). These quantities are defined as follows:

$$TPR = \frac{TP}{TP + FN} \quad (1)$$

$$FPR = \frac{FP}{FP + FN} \quad (2)$$

where TP represents true positives, FP represents false positives, and FN represents false negatives.

FIG. 6E illustrates an example precision-recall curve, precision-recall curves plot the positive predictive value (PPV, y-axis) against the true positive rate (TPR, x-axis). These quantities are defined as follows:

$$\text{precision} = PPV = \frac{TP}{TP + FP} \quad (3)$$

$$\text{recall} = TPR = \frac{TP}{TP + FN} \quad (4)$$

where TP represents true positives, FP represents false positives, and FN represents false negatives.

Based on the foregoing metrics (among others), an effectiveness or therapy efficacy rating or score may be associated with a given recommendation data object or a therapy identifier contained within a recommendation data object. Further, a cluster specific therapy efficacy rating or score may be associated with a given therapy identifier for any given cluster. Each cluster may also be evaluated and/or monitored according to metrics discussed herein for how the user states may be improving based on all recommendation data objects provided to the users of the cluster.

FIG. 9 illustrates an example data flow 900 for use with embodiments of the present disclosure. In FIG. 9, an apparatus (e.g., predictive recommendation computing entity 106 or predictive recommendation system 101) may receive, 901, originating from an external computing device (e.g., external computing entity 102), a recommendation data object request. In certain embodiments, the recommendation data object request includes a user identifier and one or more user attributes.

Data flow 900 continues with the apparatus (e.g., predictive recommendation computing entity 106 or predictive recommendation system 101) retrieving 902, based on a predictive recommendation model (e.g., and from a storage subsystem 108), one or more therapy identifiers associated with a therapy efficacy score exceeding a therapy efficacy score threshold for attributes of a first attributes set associated with a first cluster identifier. In embodiments, the first attributes set includes one or more of the one or more user attributes.

In embodiments, the predictive recommendation model is trained 904 based at least in part on trusted efficacy blocks of a distributed ledger. The trusted efficacy blocks are added to the distributed ledger when a number of therapy efficacy transaction blocks associated with a given therapy identifier and having a therapy efficacy score exceeding a therapy efficacy score threshold meets or exceeds a therapy efficacy transaction block threshold.

Data flow 900 continues with the apparatus (e.g., predictive recommendation computing entity 106 or predictive recommendation system 101) transmitting 903 (e.g., by way of a communications network), to the external computing device (e.g., external computing entity 102), a recommendation data object configured for rendering for display via a display device of the external computing device. In embodiments, the recommendation data object includes one or more of the one or more therapy identifiers.

In embodiments, the distributed ledger comprises a block chain comprising multiple transaction blocks.

In embodiments, the apparatus may further generate, based on the user identifier and the one or more user attributes, a first feature vector comprising a plurality of data records. In embodiments, each of the one or more user attributes corresponds to a unique data record of the plurality of data records. The apparatus may further assign the first feature vector to a first cluster of a plurality of clusters according to a clustering model, where the first cluster is associated with a first attributes set.

In embodiments, the apparatus may further generate one or more of a biometrics transaction block or a patient profile transaction block based on the first feature vector and add the one or more of the biometrics transaction block or the patient profile transaction block to the distributed ledger.

In embodiments, the apparatus may further add the one or more of the biometrics transaction block or the patient profile transaction block to the distributed ledger based at least in part on validating a hash of all blocks in the distributed ledger.

In embodiments, the apparatus may further receive one or more therapy feedback objects comprising a plurality of therapy feedback data records and at least one therapy identifier. The apparatus may then generate, based in part on a therapy efficacy model and the plurality of therapy feedback data records, a therapy efficacy score for the at least one therapy identifier. The apparatus may then further generate, based on the therapy efficacy score, at least one therapy identifier, and one or more therapy feedback objects, a therapy efficacy transaction block, and add the therapy efficacy transaction block to the distributed ledger.

In embodiments, the therapy efficacy model is trained based at least in part on historical patient profile data, historical patient biometric data, and known therapy efficacy data.

In embodiments, the predictive recommendation model is periodically re-trained based at least in part on new trusted efficacy blocks added to the distributed ledger.

In embodiments, the recommendation data object is associated with a recommendation category. A recommendation category is one or more of lifestyle recommendation, mindfulness activity, sleep pattern, exercise regime, workout strategy, behavioral guideline, daily routine adjustment.

In embodiments, at least one therapy identifier of the one or more therapy identifiers is associated with a recommender category. A recommender category is one or more of psychiatrist, behavioral therapist, researcher, educational institute, wellness coach, lifestyle guru, life coach.

In embodiments, the apparatus may further generate, based on the first feature vector, a plurality of other feature vectors associated with a plurality of other user identifiers retrieved from a data repository, and a clustering model, a plurality of clusters, where each cluster of the plurality of clusters comprises a plurality of feature vectors.

In embodiments, the apparatus may further generate, based on similarity scores associated with each cluster of the plurality of clusters, a plurality of sub-chains, where each sub-chain of the plurality of sub-chains comprises those clusters having similarity scores meeting or exceeding a similarity score threshold.

In embodiments, the apparatus may further receive, originating from one or more electronic sensors associated with the user identifier, biometric data associated with the user identifier, generate, based at least in part on the user identifier and the biometric data, a biometric data transaction block, add the biometric data transaction block to the distributed ledger. Biometric data comprises one or more of physiological or psychological data.

In embodiments, the therapy efficacy model is trained based at least in part on feature vectors associated with a plurality of control group objects. The plurality of control group objects are identified based at least in part on common attributes associated with clusters.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computing system comprising one or more processors and memory storing instructions that, with the one or more processors, configure the computing system to:
   train, using a supervisory training function, a machine learning collaborative filtering model, using (i) a plurality of feature vectors corresponding to a plurality of user identifiers and (ii) known therapy efficacy data, to generate a trained machine learning collaborative filtering model;
   receive, originating from an external computing device, a recommendation data object request, the recommendation data object request comprising a user identifier and one or more user attributes;
   input the one or more user attributes into the trained machine learning collaborative filtering model;
   generate, using the trained machine learning collaborative filtering model, one or more therapy identifiers associated with one or more therapy efficacy scores exceeding a therapy efficacy score threshold for one or more of the one or more user attributes;
   provide, to the external computing device and in response to the recommendation data object request, a recommendation data object comprising one or more of the one or more therapy identifiers, causing the external computing device to provide, based at least in part on the recommendation data object, a therapy feedback object for generating a therapy efficacy transaction block for a distributed ledger, wherein the therapy efficacy transaction block comprises a therapy efficacy score for the user identifier and a therapy identifier; and
   retrain, using a reinforcement learning function, the trained machine learning collaborative filtering model using (i) the plurality of feature vectors and (ii) a plurality of trusted efficacy blocks of the distributed ledger, wherein the plurality of trusted efficacy blocks is generated by:
      generating, based at least in part on a therapy efficacy model, a plurality of therapy efficacy transaction blocks based at least in part on (i) a respective therapy efficacy score and (ii) one or more respective efficacy indication objects associated with each of a plurality of therapy identifiers, and
      generating, based at least in part on an efficacy consensus protocol, a trusted efficacy block from the distributed ledger in response to a number of the plurality of therapy efficacy transaction blocks satisfying a therapy efficacy transaction block threshold.

2. The computing system of claim 1, wherein the distributed ledger comprises a block chain comprising a plurality of transaction blocks.

3. The computing system of claim 1, wherein the memory stores instructions that, with the one or more processors, further configure the computing system to:
   generate, based at least in part on the user identifier and the one or more user attributes, a first feature vector comprising a plurality of data records, wherein each of the one or more user attributes corresponds to a unique data record of the plurality of data records; and
   assign the first feature vector to a first cluster of a plurality of clusters according to a clustering model, the first cluster associated with the one or more of the one or more user attributes.

4. The computing system of claim 3, wherein the memory stores instructions that, with the one or more processors, further configure the computing system to:

generate one or more of a biometrics transaction block or a patient profile transaction block based at least in part on the first feature vector; and add the one or more of the biometrics transaction block or the patient profile transaction block to the distributed ledger.

5. The computing system of claim 4, wherein the memory stores instructions that, with the one or more processors, further configure the computing system to:

add the one or more of the biometrics transaction block or the patient profile transaction block to the distributed ledger based at least in part on validating a hash of all blocks in the distributed ledger.

6. The computing system of claim 1, wherein the memory stores instructions that, with the one or more processors, further configure the computing system to:

receive one or more therapy feedback objects comprising a plurality of therapy feedback data records and at least one therapy identifier of the one or more therapy identifiers;

generate, based in part on the therapy efficacy model and the plurality of therapy feedback data records, the therapy efficacy score for the at least one therapy identifier;

generate a therapy efficacy transaction block based at least in part on the therapy efficacy score, the at least one therapy identifier, and the one or more therapy feedback objects; and cause storage of the therapy efficacy transaction block on the distributed ledger.

7. The computing system of claim 1, wherein the therapy efficacy model is trained based at least in part on historical patient profile data, historical patient biometric data, and known therapy efficacy data.

8. The computing system of claim 1, wherein the trained machine learning collaborative filtering model is periodically re-trained based at least in part on new trusted efficacy blocks added to the distributed ledger.

9. The computing system of claim 1, wherein the recommendation data object is associated with a recommendation data object identifier.

10. The computing system of claim 1, wherein the recommendation data object is associated with a recommendation category.

11. The computing system of claim 10, wherein the recommendation category is one or more of lifestyle recommendation, mindfulness activity, sleep pattern, exercise regime, workout strategy, behavioral guideline, daily routine adjustment.

12. The computing system of claim 1, wherein at least one therapy identifier of the one or more therapy identifiers is associated with a recommender category.

13. The computing system of claim 12, wherein the recommender category is one or more of psychiatrist, behavioral therapist, researcher, educational institute, wellness coach, lifestyle guru, life coach.

14. The computing system of claim 3, wherein the memory stores instructions that, with the one or more processors, further configure the computing system to:

generate, based at least in part on the first feature vector, a plurality of other feature vectors associated with a plurality of other user identifiers retrieved from a data repository; and generate, via the clustering model, a plurality of clusters, wherein each cluster of the plurality of clusters comprises one or more other feature vectors of the plurality of other feature vectors.

15. The computing system of claim 14, wherein the memory stores instructions that, with the one or more processors, further configure the computing system to:

generate, based at least in part on similarity scores associated with each cluster of the plurality of clusters, a plurality of sub-chains, wherein each sub-chain of the plurality of sub-chains comprises one or more clusters having similarity scores meeting or exceeding a similarity score threshold.

16. The computing system of claim 1, wherein the memory stores instructions that, with the one or more processors, further configure the computing system to:

receive, originating from one or more electronic sensors associated with the user identifier, biometric data associated with the user identifier;

generate, based at least in part on the user identifier and the biometric data, a biometric data transaction block; and add the biometric data transaction block to the distributed ledger.

17. The computing system of claim 16, wherein the biometric data comprises one or more of physiological or psychological data.

18. The computing system of claim 16, wherein the one or more electronic sensors comprise one or more of wearable sensors, smart watches, fitness devices, audio recording devices, video recording devices, biometric sensors, throat patches, EEG sensors, galvanic skin reaction sensors, sweat sensors, or blood pressure sensors.

19. The computing system of claim 1, wherein the therapy efficacy model is trained based at least in part on feature vectors associated with a plurality of control group objects.

20. The computing system of claim 19, wherein the plurality of control group objects is identified based at least in part on common attributes associated with clusters.

21. A method for decentralized crowd sourced generation of recommendation data objects, the method comprising:

training, by one or more processors and using a supervisory training function, a machine learning collaborative filtering model, using (i) a plurality of feature vectors corresponding to a plurality of user identifiers and (ii) known therapy efficacy data, to generate a trained machine learning collaborative filtering model;

receiving, by the one or more processors, a recommendation data object request originating from an external computing device, the recommendation data object request comprising a user identifier and one or more user attributes;

inputting, by the one or more processors, the one or more user attributes into the trained machine learning collaborative filtering model;

generating, by the one or more processors and using the trained machine learning collaborative filtering model, one or more therapy identifiers associated with one or more therapy efficacy scores exceeding a therapy efficacy score threshold for one or more of the one or more user attributes;

providing, by the one or more processors and to the external computing device in response to the recommendation data object request, a recommendation data object comprising one or more of the one or more therapy identifiers, causing the external computing device to provide, based at least in part on the recommendation data object, a therapy feedback object for generating a therapy efficacy transaction block for a distributed ledger, wherein the therapy efficacy transaction block comprises a therapy efficacy score for the user identifier and a therapy identifier; and retraining, by the one or more processors and using a reinforcement learning function, the trained machine learning collaborative filtering model using (i) the plurality of feature vectors and (ii) a plurality of trusted efficacy blocks of the distributed ledger, wherein the plurality of trusted efficacy blocks is generated by:

generating, based at least in part on a therapy efficacy model, a plurality of therapy efficacy transaction blocks based at least in part on (i) a respective therapy efficacy score and (ii) one or more respective efficacy indication objects associated with each of a plurality of therapy identifiers, and generating, based at least in part on an efficacy consensus protocol, a trusted efficacy block from the distributed ledger in response to a number of the plurality of therapy efficacy transaction blocks satisfying a therapy efficacy transaction block threshold.

22. A computer-readable medium comprising at least one non-transitory storage medium storing instructions that, when executed by one or more processors, cause an apparatus to:

train, using a supervisory training function, a machine learning collaborative filtering model, using (i) a plurality of feature vectors corresponding to a plurality of user identifiers and (ii) known therapy efficacy data, to generate a trained machine learning collaborative filtering model;

receive, originating from an external computing device, a recommendation data object request, the recommendation data object request comprising a user identifier and one or more user attributes;

input the one or more user attributes into the trained machine learning collaborative filtering model;

generate, using the trained machine learning collaborative filtering model, one or more therapy identifiers associated with one or more therapy efficacy scores exceeding a therapy efficacy score threshold for one or more of the one or more user attributes;

provide, to the external computing device and in response to the recommendation data object request, a recommendation data object comprising one or more of the one or more therapy identifiers, causing the external computing device to provide, based at least in part on the recommendation data object, a therapy feedback object for generating a therapy efficacy transaction block for a distributed ledger, wherein the therapy efficacy transaction block comprises a therapy efficacy score for the user identifier and a therapy identifier; and retrain, using a reinforcement learning function, the trained machine learning collaborative filtering model using (i) the plurality of feature vectors and (ii) a plurality of trusted efficacy blocks of the distributed ledger, wherein the plurality of trusted efficacy blocks is generated by:

generating, based at least in part on a therapy efficacy model, a plurality of therapy efficacy transaction blocks based at least in part on (i) a respective therapy efficacy score and (ii) one or more respective efficacy indication objects associated with each of a plurality of therapy identifiers, and generating, based at least in part on an efficacy consensus protocol, a trusted efficacy block from the distributed ledger in response to a number of the plurality of therapy efficacy transaction blocks satisfying a therapy efficacy transaction block threshold.

* * * * *